(12) United States Patent
Komanduri et al.

(10) Patent No.: US 11,913,962 B2
(45) Date of Patent: Feb. 27, 2024

(54) MATERIALS AND METHODS FOR SUBJECTS AT RISK FOR VIRAL REACTIVATION

(71) Applicant: UNIVERSITY OF MIAMI, Miami, FL (US)

(72) Inventors: Krishna Komanduri, Miami, FL (US); Eric Wieder, Miami, FL (US); Jose Camargo, Miami, FL (US); Erik Kimble, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 948 days.

(21) Appl. No.: 16/613,411

(22) PCT Filed: May 14, 2018

(86) PCT No.: PCT/US2018/032577
§ 371 (c)(1),
(2) Date: Nov. 13, 2019

(87) PCT Pub. No.: WO2018/213192
PCT Pub. Date: Nov. 22, 2018

(65) Prior Publication Data
US 2020/0072848 A1 Mar. 5, 2020

Related U.S. Application Data

(60) Provisional application No. 62/506,585, filed on May 15, 2017.

(51) Int. Cl.
*G01N 33/68* (2006.01)

(52) U.S. Cl.
CPC ..... *G01N 33/6863* (2013.01); *G01N 2333/03* (2013.01); *G01N 2333/523* (2013.01); *G01N 2333/525* (2013.01); *G01N 2333/55* (2013.01); *G01N 2333/57* (2013.01); *G01N 2800/245* (2013.01)

(58) Field of Classification Search
CPC ................................................. G01N 33/6863
See application file for complete search history.

(56) References Cited

U.S. PATENT DOCUMENTS

2016/0377602 A1   12/2016   Palmer et al.

FOREIGN PATENT DOCUMENTS

| WO | 2011/119920 A2 | 9/2011 |
| WO | 2014/100853 A1 | 7/2014 |
| WO | 2015/066057 A2 | 5/2015 |

OTHER PUBLICATIONS

Geldmacher et al., Pathogen-specific T cell depletion and reactivation of opportunistic pathogens in HIV infection, Trend. Immun., 33(5):207-214 (2012).
Reikvam et al., The Pretransplantation Serum Cytokine Profile inAllogeneic Stem Cell Recipients Differs from Healthy Individuals, and Various Profiles are Associated with Different Risks of Posttransplantation Complications, Bio. Blood Marr. Trans., 18(2):190-199 (2011).
Weinberg et al., Regulatory T Cells and the Risk of CMV End-Organ Disease in Patients With AIDS, J. Acquir. Immune. Oefic. Syndr., 66(1):25-32 (2014).
Bao et al., Adoptive immunotherapy with CMV-specific cytotoxic T lymphocytes for stem cell transplant patients with refractory CMV infections, J. Immunother., 35(3):293-298 (2012).
BMT Tandem meetings, (CIBMTR working committee) infection and immune reconstitution, Gaylord palms convention center, Feb. 25, 2017, 1 page.
BMT Tandem meetings, Pivotal phase 2 trial of Kte-C19 (anti-CD19 CAR T cells) in patients with refractory aggressive NHL (ZUMA-1), Gaylord palms convention center, Feb. 26, 2017, 4 pages.
Casazza et al., Acquisition of direct antiviral effector functions by CMV-specific CD4+ T lymphocytes with cellular maturation, J. Exp. Med., 123(13):2865-2877 (2006).
Casazza et al., Autocrine production of beta-chemokines protects CMV-Specific CD4 T cells from HIV infection, PLoS. Pathog., 5(10):1-13 (2009).
Chiuppesi et al., Identification of a continuous neutralizing epitope with in UL 128 of human cytomegalovirus, J. Virology, Accepted manuscript posted online Jan. 11, 2017.
Feuchtinger et al., Adoptive transfer of pp65-specific T cells for the treatment of chemorefractory cytomegalovirus disease or reactivation after haploidentical and matched unrelated stem cell transplantation, Blood, 116(20):4360-4367 (2010).
Feuchtinger, CMV: persistent nemesis for SCT, Blood, 127(20):2368-2369 (2016).
International Application No. PCT/US18/32577, International Preliminary Report on Patentability, dated Nov. 28, 2019.
International Application No. PCT/US18/32577, International Search Report and Written Opinion, dated Aug. 23, 2018.
Kim et al., Human late memory CD8+ T cells have a distinct cytokine signature characterized by CC chemokine production without IL-2 production, J. Immunol., 183:6167-6174 (2009).
Komanduri et al., Direct measurement of CD4+ and CD8+ T-cell responses to CMV in HIV-1-infected subjects, Virology, 279(2):459-70 (2001).
Komanduri et al., Restoration of cytomegalovirus-specific CD4+ T-lymphocyte responses after ganciclovir and highly active antiretroviral therapy in individuals infected with HIV-1, Nat. Med., 4(8):953-956 (1998).

(Continued)

*Primary Examiner* — Prema M Mertz
(74) *Attorney, Agent, or Firm* — MARSHALL, GERSTEIN & BORUN LLP

(57) ABSTRACT

Described herein are materials and methods for stratifying risk for reactivation of a latent viral infection, such as CMV infection. The methods are particularly useful for immune compromised subjects. Also described herein are interventions, including therapeutic, prophylactic, and monitoring interventions, for subjects determined to be at elevated risk.

12 Claims, 21 Drawing Sheets
Specification includes a Sequence Listing.

(56) References Cited

OTHER PUBLICATIONS

Kraft et al., Interpreting quantitative cytomegalovirus DNA testing: Understanding the laboratory perspective, Clinical Infections Diseases, 54(12):1793-97 (2012).

Merck, Merck announces pivotal phase 3 study of letermovir, an investigational antiviral medicine for prevention of cytomegalovirus (CMV) infection in high-risk bone marrow transplant patients, met primary endpoint, Published on, (https://www.mrknewsroom.com) on Oct. 19, 2016.

Nakamura et al., Cytomegalovirus chimeric epitope vaccine supplemented with PF03512676 (CMVPepVax) in allogeneic hematopoietic stem cell transplantation: viremia, immunogenicity and survival outcomes in a randomised phase 1b trial, Lancet Haematol., 3(2):e87-e98 (2016).

Nesher et al., Utility of the enzyme-linked immunospot interferon-gamma-release assay to predict the risk of cytomegalovirus infection in hematopoietic cell transplant recipients, J. Infect. Dis., 13(11):1701-7 (2016).

O'Donnell et al., Multiparameter flow cytometry: Advances in high resolution analysis, Immune Network, 13(2):43-54 (2013).

Ozdemir et al, Risk factors associated with late cytomegalovirus reactivation after allogeneic stem cell transplantation for hematological malignancies, Bone Marrow Transplant., 40(2):125-36 (2007).

Ozdemir et al., A model to predict risk for late cytomegalovirus reactivation after allogeneic stem cell transplantation for hematological malignancies, Blood, 104(11):2241 (2004).

Ozdemir et al., Cytomegalovirus reactivation following allogeneic stem cell transplantation is associated with the presence of dysfunctional antigen-specific CD8+ T cells, Blood, 100:3690-3697 (2002).

Preiksaitis et al., Are we there yet? Impact of the first international standard for cytomegalovirus DNA on the harmonization of results reported on plasma samples, CID, 63:583-589 (2016).

Schwartz, Direct visualization of antigen-specific cytotoxic T cells—a new insight into immune defenses, The New England Journal of Medicine, 339(15):1076-1078 (1998).

Seder et al., T-cell quality in memory and protection: implications for vaccine design, Nature Reviews Immunology, 8:247-258 (2008).

Snyder et al., Polyfunctional T-cell signatures to predict protection from cytomegalovirus after lung transplantation, Am. J. Respir. Crit. Care Med., 193(1):78-85 (2016).

Teira et al., Early cytomegalovirus reactivation remains associated with increased transplant-related mortality in the current era: a CIBMTR analysis, Blood, 127(20):2427-2438 (2016).

The et al., Cytomegalovirus Antigenemia, Rev. Infect. Dis., 12:S734-744 (1990).

Walter et al., Reconstitution of cellular immunity against cytomegalovirus in recipients of allogeneic bone marrow by transfer of T-cell clones from the donor, N. Engl. J. Med., 333:1038-1044 (1995).

```
                          SEQUENCE LISTING

<160> NUMBER OF SEQ ID NOS: 4

<210> SEQ ID NO 1
    <211> LENGTH: 153
    <212> TYPE: PRT
    <213> ORGANISM: Homo sapiens
    <220> FEATURE:
    <221> NAME/KEY: MISC_FEATURE
    <223> OTHER INFORMATION: IL-2

<400> SEQUENCE: 1

Met Tyr Arg Met Gln Leu Leu Ser Cys Ile Ala Leu Ser Leu Ala Leu
    1               5                   10                  15

Val Thr Asn Ser Ala Pro Thr Ser Ser Ser Thr Lys Lys Thr Gln Leu
                    20                  25                  30

Gln Leu Glu His Leu Leu Leu Asp Leu Gln Met Ile Leu Asn Gly Ile
                35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
    65                  70                  75                  80

Glu Glu Leu Lys Pro Leu Glu Glu Val Leu Asn Leu Ala Gln Ser Lys
                    85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
        130                 135                 140

Cys Gln Ser Ile Ile Ser Thr Leu Thr
    145                 150

<210> SEQ ID NO 2
    <211> LENGTH: 166
    <212> TYPE: PRT
    <213> ORGANISM: Homo sapiens
    <220> FEATURE:
    <221> NAME/KEY: MISC_FEATURE
    <223> OTHER INFORMATION: INF-gamma

<400> SEQUENCE: 2

Met Lys Tyr Thr Ser Tyr Ile Leu Ala Phe Gln Leu Cys Ile Val Leu
    1               5                   10                  15
```

```
Gly Ser Leu Gly Cys Tyr Cys Gln Asp Pro Tyr Val Lys Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
 50                  55                  60

Arg Lys Ile Met Gln Ser Gln Ile Val Ser Phe Tyr Phe Lys Leu Phe
 65                  70                  75                  80

Lys Asn Phe Lys Asp Asp Gln Ser Ile Gln Lys Ser Val Glu Thr Ile
                 85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 3
<211> LENGTH: 233
<212> TYPE: PRT
<213> ORGANISM: Homo sapiens
<220> FEATURE:
<221> NAME/KEY: MISC_FEATURE
<223> OTHER INFORMATION: TNF-alpha

<400> SEQUENCE: 3

Met Ser Thr Glu Ser Met Ile Arg Asp Val Glu Leu Ala Glu Glu Ala
 1               5                  10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
 50                  55                  60

Arg Asp Leu Ser Leu Ile Ser Pro Leu Ala Gln Ala Val Arg Ser Ser
 65                  70                  75                  80

Ser Arg Thr Pro Ser Asp Lys Pro Val Ala His Val Val Ala Asn Pro
                 85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205
```

```
Ser Ala Glu Ile Asn Arg Pro Asp Tyr Leu Asp Phe Ala Glu Ser Gly
    210                 215                 220

Gln Val Tyr Phe Gly Ile Ile Ala Leu
225             230

<210> SEQ ID NO 4
<211> LENGTH: 92
<212> TYPE: PRT
<213> ORGANISM: Homo sapiens
<220> FEATURE:
<221> NAME/KEY: MISC_FEATURE
<223> OTHER INFORMATION: MIP-1Beta

<400> SEQUENCE: 4

Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
                20                  25                  30

Ala Cys Cys Phe Ser Tyr Thr Ala Arg Lys Leu Pro Arg Asn Phe Val
            35                  40                  45

Val Asp Tyr Tyr Glu Thr Ser Ser Leu Cys Ser Gln Pro Ala Val Val
    50                  55                  60

Phe Gln Thr Lys Arg Ser Lys Gln Val Cys Ala Asp Pro Ser Glu Ser
65                  70                  75                  80

Trp Val Gln Glu Tyr Val Tyr Asp Leu Glu Leu Asn
                85                  90
```

MATERIALS AND METHODS FOR SUBJECTS AT RISK FOR VIRAL REACTIVATION

CROSS REFERENCE TO RELATED APPLICATIONS

This application is a US national stage of International Patent Application No. PCT/US2018/032577, filed on 14 May 2018, which claims priority under § 119 to US Provisional Patent Application No. 62/506,585, filed on 15 May 2017.

INCORPORATION BY REFERENCE OF MATERIAL SUBMITTED ELECTRONICALLY

A Sequence Listing is incorporated herein by reference as part of the disclosure. The sequence listing was submitted as a text file named "52000A_Seqlisting.txt", which was created on Nov. 13, 2019, and is 6,274 bytes in size.

FIELD OF THE INVENTION

The invention relates to infectious disease prevention and treatment. More particularly, the invention relates to care for immune-compromised subjects, such as transplant subjects, at risk for reactivation of a latent viral infection.

BACKGROUND

Cytomegalovirus (CMV) reactivation occurs in up to 60-80% of CMV seropositive allogeneic (hematopoietic cell transplant, HCT) recipients, and is associated with significant morbidity and mortality. See, e.g., Teira et al., "Early cytomegalovirus reactivation remains associated with increased transplant-related mortality in the current era: a CIBMTR analysis," Blood 2016 :blood-2015-11-679639; doi: https://doi.org/10.1182/blood-2015-11-679639. Despite the availability of antiviral therapies, CMV reactivation remains associated with increased risk of non-relapse mortality and poorer overall survival in the modern era. Functional assessments to try and predict risk of CMV reactivation have been developed, but have been poorly predictive and are therefore not considered standard-of-care. The availability of a predictive assay would allow closer surveillance of individuals at highest risk and/or avoidance of potentially costly prophylaxis strategies that are under development.

To the date, no highly predictive biomarkers for accurate prediction of CMV reactivation following HCT exist. Well tolerated antivirals that can be used to prevent CMV infection are expected to be on the market soon but likely to be expensive, and it is unclear which patients will benefit from prophylaxis with such agents, because not all CMV-seropositive recipients experience viral reactivation.

Furthermore, these needs are not limited to HCT patents and CMV reactivation. A need exists for assays suitable to predict reactivation (or stratify risk for reactivation) of other latent viruses besides CMV, and to do this for other immune-compromised besides HCT recipients.

SUMMARY OF THE INVENTION

As described herein, the invention provides materials and methods that can improve health care and outcomes for immune-compromised subjects, such as transplant subjects, at risk for reactivation of latent viral infections. The invention also provides materials and methods for T cell analysis in a new and informative manner. Much of the invention is described herein with reference to CMV infection, which is intended as only one exemplary embodiment of the full breadth of the invention.

The invention further includes novel materials and methods for prophylaxis and therapy for viral infections, and new uses for existing antiviral treatment agents.

Additional embodiments and aspects of the invention are reflected in the following numbered paragraphs:

1. A method comprising:
   identifying or quantifying a risk for reactivation of a latent virus in an immune-compromised mammalian subject from measurements of a T cell subset from a sample isolated from the subject, wherein the T cell subset is identifiable from a cytokine expression profile of cytokines interleukin-2 (IL-2), interferon gamma (IFNγ), tumor necrosis factor alpha (TNFα), and macrophage inflammatory protein 1β (MIP-1β).
2. Use of measurements of expression of a T cell subset from a sample isolated from an immune-compromised mammalian subject to identify or quantify a risk for reactivation of a latent virus in the subject, wherein the T cell subset is identifiable from a cytokine expression profile of cytokines interleukin-2 (IL-2), interferon gamma (IFNγ), tumor necrosis factor alpha (TNFα), and macrophage inflammatory protein 1β (MIP-1β).
3. The method or use according to paragraph 1 or 2 that comprises detecting or measuring expression of IL-2, IFNγ, TNFα, and MIP-1β in individual T cells from the sample.
4. The method or use according to paragraph 3 that comprises measuring cytokine expression by measuring mRNA encoding the cytokines in the T cells, or measuring cytokine proteins on or in the T cells.
5. The method or use according to paragraph 3, comprising measuring cytokine expression with flow cytometry, mass cytometry, imaging cytometry, or slide scanning cytometry.
6. The method or use according to paragraph 3, comprising measuring cytokine expression with multiparameter flow cytometry.
7. The method or use according to any one of paragraphs 1-6, wherein the mammalian subject is human.
8. The method or use according to any one of paragraphs 1-7, wherein the subject is a transplant recipient.
9. The method or use according to paragraph 8, wherein the transplant recipient is an allogeneic transplant recipient.
10. The method or use according to paragraph 8 or 9, wherein the transplant recipient is an organ transplant recipient, a tissue transplant recipient, or a cell transplant recipient.
11. The method or use according to any one of paragraphs 8-10, wherein the subject is a hematopoietic cell transplant recipient.
12. The method or use according to paragraph 11, wherein the subject is a stem cell recipient or a bone marrow transplant recipient.
13. The method or use according to any one of paragraphs 8-12, wherein the identifying or quantifying risk is performed on a sample comprising the T cells obtained from the subject 7-50 days after the transplant.
14. The method or use according to any one of paragraphs 8-12, wherein the identifying or quantifying risk is performed on a sample comprising the T cells obtained from the subject 8-40 days after the transplant.

15. The method or use according to any one of paragraphs 8-12, wherein the identifying or quantifying risk is performed on a sample comprising the T cells obtained from the subject 10-30 days after the transplant.
16. The method or use according to any one of paragraphs 8-12, wherein the identifying or quantifying risk is performed on a sample comprising the T cells obtained from the subject 14, 15, 16, 17, 18, 19, 20, 21, 22, 23, 24, 25, 26, 27, 28, 29, or 30 days after the transplant.
17. The method or use according to any one of paragraphs 1-16, wherein the subject is immune-compromised from cancer chemotherapy.
18. The method or use according to any one of paragraphs 1-17, wherein the subject is immune-compromised from immunosuppressant therapy.
19. The method or use according to any one of paragraphs 1-18, wherein the sample is a cryopreserved sample comprising T cells.
20. The method or use according to any one of paragraphs 1-19, wherein the sample is a never-frozen sample comprising T cells.
21. The method or use according to any one of paragraphs 1-20, wherein the viral reactivation comprises reactivation of a latent herpesviridae virus.
22. The method or use according to paragraph 21, wherein the herpesviridae virus comprises an Epstein Barr Virus (EBV or HHV-4), a Varicella zoster virus (VZV), a herpes simplex virus (HSV), a human herpesvirus 6 (HHV-6), a cytomegalovirus (CMV or HHV-5), or a Kaposi's sarcoma-associated herpesvirus (KSHV or HHV-8).
23. The method or use according to paragraph 21, wherein the herpesviridae virus is a CMV.
24. The method or use according to any one of paragraphs 21-23 that comprises measuring of the expression of the cytokines by:
exposing the T cells to one or more antigens from the latent herpesviridae virus, under conditions to stimulate a T cell immune response;
evaluating individual T cells for a cytokine expression phenotype after the exposing step, the cytokine expression phenotype of a T cell indicative of which of the cytokines are expressed by the T cell; and
quantifying T cells having at least one cytokine expression phenotype.
25. The method or use according to paragraph 24 that further comprises evaluating individual T cells for CD4 expression or CD8 expression.
26. The method or use according to paragraph 24 or 25 that comprises:
quantifying CD8-positive (CD8+), IL-2-positive (IL-2+), IFNγ-positive (IFNγ+), TNFα-positive (TNFα+), MIP-1β-positive (MIP-1β+) T cells ("PHENOTYPE-P") from the sample, or
quantifying CD8-positive (CD8+), IL-2-negative (IL-2−), IFNγ-positive (IFNγ+), TNFα-negative (TNFα−), MIP-1β-positive (MIP-1β+) T cells ("PHENOTYPE-N") from the sample.
27. The method or use according to paragraph 26, that comprises quantifying PHENOTYPE-P T cells and quantifying PHENOTYPE-N T cells from the sample.
28. The method or use according to any one of paragraphs 24-27, wherein the evaluating step comprises:
contacting the T cells after the exposing step with cytokine-specific agents to identify expression of each of the cytokines in the T cells; and
determining cytokine expression from interaction of intracellular cytokine(s) with the cytokine-specific agents in the cells.
29. The method or use according to any one of paragraphs 24-28, wherein the evaluating step comprises:
staining intracellular cytokines expressed in the T cells after the exposing, wherein each of the cytokines is stained with a cytokine-specific agent to uniquely identify the cytokine, and
determining expression of a cytokine from intracellular staining by the cytokine-specific agent that uniquely identifies the cytokine.
30. The method or use according to paragraph 29, wherein the staining step comprises fixing the T cells, permeabilizing the T cells to the cytokine-specific agents, and staining the intracellular cytokines with the cytokine-specific agents.
31. The method or use according to paragraph 29 or 30, wherein the cytokine-specific agents comprise cytokine-specific antibodies, or antigen binding fragments thereof.
32. The method or use according to paragraph 31, wherein each cytokine-specific antibody, or antigen binding fragment thereof, includes a unique detectable label, to permit detection of each cytokine by detection of the unique label.
33. The method or use according to any one of paragraphs 24-32, wherein the one or more antigens comprises a viral envelope protein antigen, or comprises one or more antigenic fragments thereof.
34. The method or use according to any one of paragraphs 24-32, wherein the latent virus is CMV, and the one or more antigens comprises CMV tegument phosphoprotein 65 (pp65), or CMV immediate early 1 (1E1) protein, or comprises one or more antigenic fragments thereof, or comprises mixtures of said proteins or antigenic fragments.
35. The method or use according to any one of paragraphs 24-34, wherein the exposing of the T cells to the one or more antigens comprises:
isolating peripheral blood mononuclear cells (PBMC) from the sample, and incubating the PBMC with the one or more antigens.
36. The method or use according to paragraph 35 that comprises extracting the PBMC from the sample using ficoll gradient centrifugation.
37. The method or use according to paragraph 36, wherein the exposing is for a period of 4-16 hours.
38. The method or use according to paragraph 36, wherein the exposing is for a period of 5-8 hours.
39. The method or use according to any one of paragraphs 24-34 that comprises lysing of red blood cells in the sample prior to exposing the T cells to the one or more antigens.
40. The method or use according to any one of paragraphs 24-34 that comprises isolating T cells from the sample, and incubating the isolated T cells with the one or more antigens, wherein the one or more antigens are peptide antigens from the latent herpesviridae virus.
41. The method or use according to any one of paragraphs 24-40, wherein the exposing step further comprises exposing the T cells to anti-CD49d and/or anti-CD28 antibodies.
42. The method or use according to any one of paragraphs 24-41, wherein the quantifying of the T cells having at least one cytokine expression phenotype comprises measurement of the cytokine expression by flow cytometry.
43. The method or use according to any one of paragraphs 24-42, wherein the quantifying comprises quantifying the T cells with the phenotype relative to total T cells analyzed, to generate a relative measure of the quantity of the T cells with the phenotype.
44. The method or use according to paragraph 28, wherein the cytokine-specific agents are probes for detecting cytokine mRNAs in the T-cells.
45. The method or use according to any one of paragraphs 26-44, wherein increased percentages of Phenotype-N T cells in the sample are correlated with increased risk of viral reactivation in the subject, and decreased percentages of Phenotype-N T cells in the sample are correlated with decreased risk of viral reactivation in the subject.
46. The method or use according to any one of paragraphs 26-44, wherein increased percentages of Phenotype-P T cells in the sample are correlated with decreased risk of viral reactivation in the subject, and decreased percentages of Phenotype-P T cells in the sample are correlated with increased risk of viral reactivation in the subject.
47. The method or use according to any one of paragraphs 26-46 wherein the combination of a high percentage of Phenotype-P T cells and a low percentage of Phenotype-N T cells in the sample are correlated with low risk of viral reactivation in the subject.
48. The method or use according to any one of paragraphs 26-46, wherein the combination of a high percentage of Phenotype-N T cells and a low percentage of Phenotype-P T cells in the sample are correlated with high risk of viral reactivation in the subject.
49. The method or use according to any one of paragraphs 26-44 that comprises:
(a) detecting elevated percentages of Phenotype-N T cells in the sample, and diagnosing the subject as having an increased risk of viral reactivation; or
(b) detecting a low percentage of Phenotype-N T cells in the sample, and diagnosing the subject as having decreased risk of viral reactivation.
50. The method or use according to any one of paragraphs 26-44 that comprises:
(a) detecting a high percentage of Phenotype-P T cells in the sample, and diagnosing the subject as having a decreased risk of viral reactivation; or
(b) detecting a low percentage of Phenotype-P T cells in the sample, and diagnosing the subject as having increased risk of viral reactivation.
51. The method or use according to any one of paragraphs 26-44 that comprises detecting a combination of a high percentage of Phenotype-P T cells and a low percentage of Phenotype-N T cells in the sample, and diagnosing the subject as having a low risk of viral reactivation.
52. The method or use according to any one of paragraphs 26-44 that comprises detecting a combination of a high percentage of Phenotype-N T cells and a low percentage of Phenotype-P T cells in the sample, and diagnosing the subject as having a high risk of viral reactivation.
53. The method or use according to any one of paragraphs 1-52, further comprising prescribing or administering, to a subject identified as having elevated or high risk of viral reactivation according to any one of paragraphs 1-52, a prophylaxis that comprises an antiviral chemotherapeutic agent or an antiviral cellular therapy.
54. Use of an antiviral chemotherapeutic agent or an antiviral cellular therapy for prophylaxis in a subject identified as having a high risk of viral reactivation according to any one of paragraphs 1-52.
55. The method or use according to any one of paragraphs 53-54, wherein the prophylaxis comprises an antiviral chimeric antigen receptor T cells (CART) cellular therapy, a T cell receptor transgenic cell, or a polyclonal T cell line stimulated ex vivo with viral antigen to enrich and expand virus-specific T cells.
56. The method or use according to any one of paragraphs 53-55, wherein the prophylaxis comprises an antiviral chemotherapeutic agent.
57. The method or use according to paragraph 56, wherein the chemotherapeutic comprises at least one of Ganciclovir (Cytovene-IV), Valganciclovir (Valcyte), Foscarnet (Foscavir), Cidofovir (Vistide), Maribavir, Brincidofovir (CMX001), and Letermovir.
58. A method of prophylaxis for viremia comprising prescribing or administering, to a human transplant subject determined to have high risk for viral reactivation according to the method of any one of paragraphs 1-52, prophylaxis that comprises an antiviral chemotherapeutic agent, an antiviral vaccine, or an antiviral cellular therapy.
59. A method of monitoring an immune-compromised subject for reactivation of a latent virus, the method comprising
monitoring viral load in the peripheral blood of the subject, and
identifying or quantifying a risk for viral reactivation according to any one of paragraphs 1-52.
60. Use of monitoring of viral load, in combination with use of measurements of a T cell subset according to any one of paragraphs 1-52, to monitor an immune-compromised subject for reactivation of a latent virus.
61. The method or use according to paragraph 59 or 60, wherein the monitoring of the viral load is performed on a periodic basis, and
wherein, if the subject is identified as having high risk for viral reactivation, the frequency of monitoring of the viral load is increased by 50-200%.
62. The method or use according to any one of paragraphs 59-61, wherein monitoring of viral load comprises measuring virus in a blood, serum, or plasma sample from the subject.
63. The method or use according to paragraph 62, wherein the measuring of virus comprises quantitative PCR to measure viral nucleic acid in the sample.
64. The method or use according to any one of paragraphs 61-63, further comprising administering an antiviral therapeutic agent to a subject that exhibits increasing viral load from the monitoring and that exhibits the elevated risk for the viral reactivation.
65. The method according to any one of paragraphs 59-63, wherein the monitoring of the viral load is performed on a periodic basis, and
wherein, if the subject is identified as having low risk for viral reactivation, the frequency of monitoring of the viral load is decreased by 50-200%.
66. A method of T cell analysis comprising: staining T cells from a sample from a mammalian subject with cytokine-specific markers to identify T cell subsets based on a cytokine expression profile of cytokines interleukin-2 (IL-2), interferon gamma (IFNγ), tumor necrosis factor alpha (TNFα), and macrophage inflammatory protein 1β (MIP-1β). In some variations, the subject is an immune-compromised mammalian subject.

67. The method according to paragraph 66, further comprising quantifying T cell subsets based on the cytokine expression profile of said cytokines.
68. The method according to paragraph 66 or 67, comprising stimulating the T cells with a viral antigen prior to staining with cytokine-specific markers.
69. The method according to any one of paragraphs 66-68, further comprising calculation of a percentage of cells with a particular cytokine expression profile relative to a percentage of T cells having other cytokine expression profile(s).
70. The method according to paragraph 69 that comprises calculating a relative percentage of either
    CD8-positive (CD8+), IL-2-positive (IL-2+), IFNγ-positive (IFNγ+), TNFα-positive (TNFα+), MIP-1β-positive (MIP-1β+) T cells ("PHENOTYPE-P") from the sample, or
    CD8-positive (CD8+), IL-2-negative (IL-2−), IFNγ-positive (IFNγ+), TNFα-negative (TNFα−), MIP-1β-positive (MIP-1β+) T cells ("PHENOTYPE-N") from the sample.
71. The method according to any one of paragraphs 66-70, further comprising monitoring viral load in a sample from the subject.

Aspects of the invention that have been described herein as methods also can be described as "uses," and all such uses are contemplated as aspects of the invention. Likewise, compositions described herein as having a "use" can alternatively be described as processes or methods of using, which are contemplated as aspects of the invention.

Reference throughout this specification to "one embodiment," "some embodiments," or "an embodiment" means that a particular feature, structure or characteristic described in connection with the embodiment is included in at least one embodiment of the present disclosure. The particular features, structures, or characteristics described herein may be combined in any suitable manner, and all such combinations are contemplated as aspects of the invention.

Unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

The headings herein are for the convenience of the reader and not intended to be limiting. Additional aspects, embodiments, and variations of the invention will be apparent from the Detailed Description and/or Drawing and/or claims.

Although the Applicant invented the full scope of the invention described herein, the Applicant does not intend to claim subject matter described in the prior art work of others. Therefore, in the event that statutory prior art within the scope of a claim is brought to the attention of the Applicant by a Patent Office or other entity or individual, the Applicant reserves the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWING

FIG. 5A) and protective (PS; FIG. 5B) in CD8+ T cells grouped by CMV outcome.

DETAILED DESCRIPTION

Figure 1:
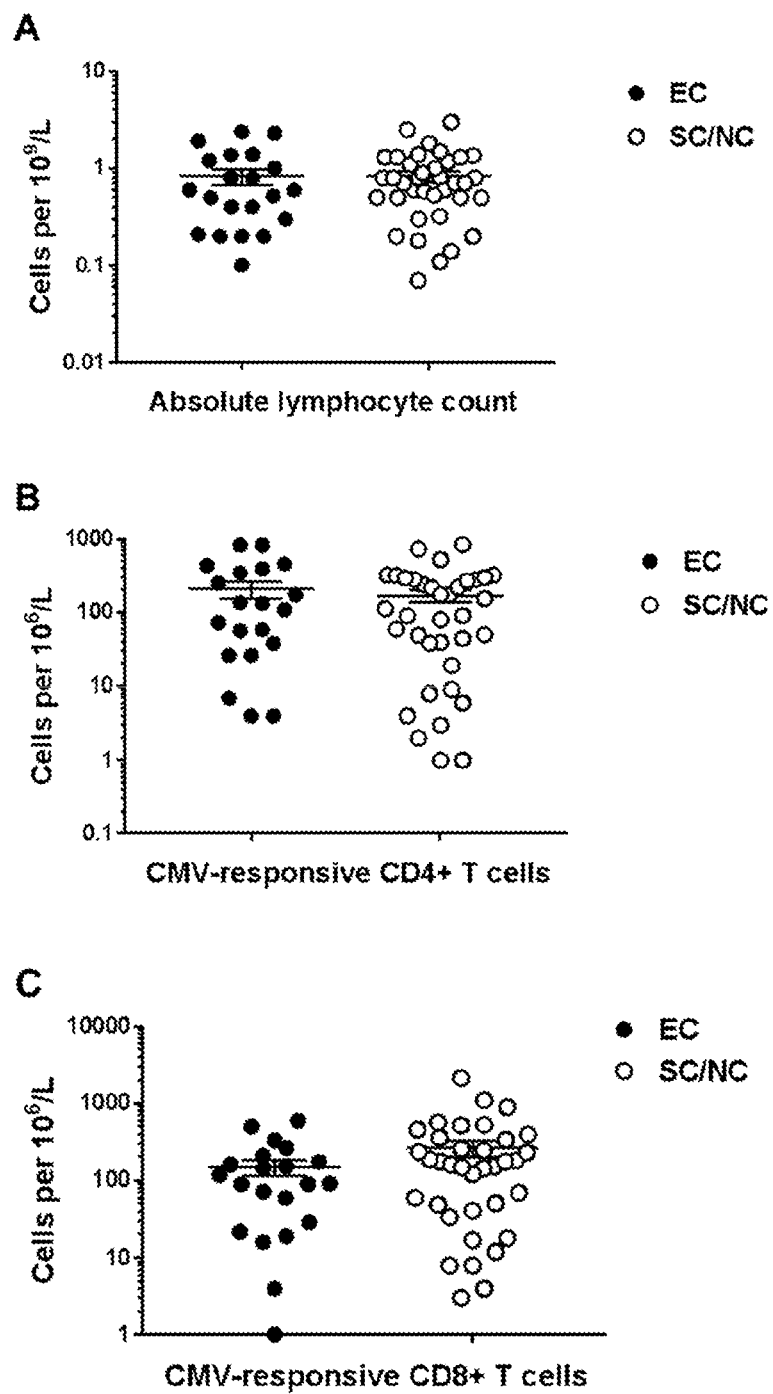
FIGS. 1A-1C are scatter plots depicting absolute lymphocyte count (FIG. 1A), absolute number of CMV-responsive CD4+ (FIG. 1B) and CD8+ (FIG. 1C) T cells, grouped by CMV outcome.

Described herein are materials and methods for stratifying risk for reactivation of a latent viral infection, such as a CMV infection. The methods are particularly useful for immune compromised subjects because such subjects are already at greater risk for viral reactivation (and its complications) than the general population. Despite higher relative risk than the general population, the immune compromised population will not uniformly suffer from viral reactivation and its complications. The materials and methods described herein can be used to stratify risk within the immune compromised population that has its own elevated baseline risk. Also described herein are interventions, including therapeutic, prophylactic, and monitoring interventions, for subjects determined to be at elevated risk.

Definitions

In the absence of specific definitions herein, terms should be construed as they would be understood by clinicians and scientists in the field of the invention.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to."

Aspects of the invention pertain to identifying or quantifying risk. In some variations, the risk can be quantified numerically as an absolute risk. For instance, based on comparison to patient data sets obtained according to techniques described herein, it is possible to assign a numerical risk score, such as a probability of experiencing an event (e.g., virus reactivation or progressive viremia) within a certain period of time.

In some variations, risk assessment is a relative risk assessment. For instance, a subject has a baseline risk for an event (e.g., virus reactivation or progressive viremia) by virtue of belonging to a recognized class (e.g., a patient that has received a hematopoietic cell transplant within the past month). The materials and methods described herein are useful for stratifying individuals within such a class as having elevated or increased risk, compared to the baseline risk of the hematopoietic cell transplant group of patients as a whole; or a reduced or decreased risk, compared to the baseline risk. Relative risk can be expressed quantitatively also (e.g., percent greater risk than the baseline or an odds ratio). Generally speaking, increased susceptibility or increased risk is descriptive of a relative risk or odds ratio greater than 1, compared to the baseline population. Thus, in particular embodiments of the invention, the increased susceptibility or increased risk is characterized by a relative risk of at least 1.5, including a relative risk of at least 2.0, a relative risk of at least 2.5, a relative risk of at least 3.0, a relative risk of at least 3.5, and a relative risk of at least 4.0, 4.5, 5, 5.5, 6, 7, 8, 9, 10 or more. Other embodiments are characterized by relative risk of at least 1.25, 1.75, 2.25, 2.75, 3.25, 3.75, and so on. Conversely, decreased susceptibility or decrease risk is descriptive of a relative risk or odds ratio less than 1.0. Decreased susceptibility in particular embodiments is characterized by a relative risk of less than 0.8, a relative risk of less than 0.7, a relative risk of less than 0.6, a relative risk of less than 0.5, a relative risk of less than 0.4, a relative risk of less than 0.35, a relative risk of less than 0.3, and a relative risk of less than 0.25, a relative risk of less than 0.1, and so on. These numbers are exemplary only, and will vary depending on the population chosen. The techniques described herein permit stratification of subjects to reveal and calculate a relative risk. Standard statistical techniques can be used to verify the statistical significance of the risk assessment.

In the context of methods of the invention, "prescribing" refers to providing an order or authorization for the therapy for a particular subject, wherein the therapy is then administered to that subject by person(s) and/or device(s) pursuant to the prescribing order/authorization. The physical act of administering may be by the hand of the prescribing authority; by one or more medical professionals different from the prescribing professional; self-administration by the subject or subject's caregiver (e.g., following dispensing to the subject by a pharmacy); or some combination thereof.

Aspects of the invention relate to T cell subsets that are identifiable from a cytokine expression profile of cytokines interleukin-2 (IL-2), interferon gamma (IFNγ), tumor necrosis factor alpha (TNFα), and macrophage inflammatory protein 1β (MIP-1β). In some variations, the identifying is by direct measuring of these cytokines. In some variations, the same T cell subset is identified by one or more surrogate markers that are useful for identifying the same (or practically the same) T cell subset. Having described informative T cell subsets herein, it is possible to screen such subsets for surrogate markers that are effective for identifying the subset and identifying/stratifying risk as described herein.

The term "T cell subset" refers to a portion of a subject's T cells that can be uniquely identified by a marker or set of markers expressed by those cells. For instance, as described below in greater detail, in the context of expression of a set for N markers, a population of T cells can be assigned to $2^N$ subsets. In one of the subsets, none of the markers are expressed. In the other ($2^N$-1) subsets, at least one marker is actively expressed. In some variations, the calculation of the percentage of T cells falling within a T cell subset, relative to total T cells in the $2^N$ subsets, or total T cells in the active ($2^N$-1) subsets, is contemplated.

Mammalian Subjects

The methods described herein can be practiced with any mammalian subject susceptible to viral infection, including laboratory animals (e.g., mice, rats, rabbits); livestock animals (e.g., porcine, bovine); and zoo and pet/domesticated animals (e.g., elephants, canines, felines, giraffes, equines).

In some embodiments, the subject is a primate.

In preferred embodiments, the subject is a human subject.

The analytical methods described herein are particularly useful for human subjects who harbor a latent viral infection, because the methods can stratify risk for reactivation of the latent virus. In some variations, a subject can be pre-screened for evidence of the latent virus. However, the prevalence of some latent viruses is so high in many populations that, in some variations, the presence of the virus simply can be presumed. Such viruses include Epstein-Barr virus (implicated in mononucleosis and some cancers), cytomegalovirus, and varicella zoster virus (chick pox, shingles).

Immune-Compromised Subjects

The analytical methods described herein are particularly useful for assessment for subjects that are immune-compromised. In some variations, the subject is immune compromised as a result of medications. For instance, a subject may be immune compromised from a cancer chemotherapy with cytotoxic side-effects on the subject's immune cells. (Exemplary agents with reported increased risk of CMV include Ruxolitinib and Dasatinib.) A subject may be immune compromised from immunosuppressant therapies prescribed to treat an autoimmune disease or its symptoms. A subject may be immune compromised from immunosuppressant therapies prescribed to prevent graft versus host disease (GVHD) in a transplant recipient, especially an allogeneic transplant recipient. The transplant recipient can be an organ transplant recipient, a tissue transplant recipient, or a cell transplant recipient.

In some variations, the subject has received a blood stem cell/hematopoietic progenitor cell transplant and is immune compromised at least for the reason that the transplanted cells have not fully grafted and reconstituted a fully functioning immune system. In some variations, the progenitor cell transplant is a cord blood/progenitor cell transplant.

The analytical approach described herein is particularly useful for screening subjects during the period that they are most immune compromised. For example, testing a hematopoietic progenitor transplant patient as soon as the transplant has engrafted and a testable level of T cells exists is contemplated. For example, testing 7, 8, 9, 10, 11, 12,13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 days after the transplant is contemplated. Testing during later time periods, e.g., 51-60, 61-70, 71-80, 81-90, or more days post-transplantation if the subject remains immune compromised is possible.

For cancer chemotherapy patients or patients receiving antibody therapy, testing any integer number of days from 0-50 after receipt of a cytotoxic chemotherapeutic dose is contemplated. In some variations, the testing is performed periodically any integer number of days from 0-50 after a final dose of a cytotoxic chemotherapeutic agent is administered.

The method described herein also is suitable for testing subjects that receive autoimmune immunosuppressant therapies. Exemplary therapies include Humira, Etanercept, Infliximab, other anti-TNF therapies, and other anti-inflammatory cytokine therapies. Testing according to the invention can be performed at least once, or periodically, after such therapies have initiated. Testing any integer number of days from 0-50 after a first dose is especially contemplated.

Viral Infections

The analytical techniques described herein can, in principle, be used to predict risk for reactivation of any latent virus.

In some embodiments, the virus is from the family herpes viridae (herpes viruses), a large family of DNA viruses that infect multiple species and cause diseases of varying severity. Herpes viruses that infect humans include: herpes simplex viruses 1 and 2 (HSV-1/HHV-1 and HSV-2/HHV2), varicella-zoster virus (VZV/HHV-3), Epstein-Barr virus (EBV/HHV-4), human cytomegalovirus (CMV or HCMV/HHV-5), human herpesvirus 6A and 6B (HHV-6A and HHV-6B), human herpesvirus 7 (HHV-7), and Kaposi's sarcoma-associated herpesvirus (KSHV/HHV-8).

In other variations, the virus is an immunodeficiency virus (e.g., HIV) or a hepatitis virus (e.g., HBV, HCV).

Biological Samples

The analytical methods described herein are performed with T cells.

In some variations, a tissue or fluid sample (most typically a blood sample) from the subject is used as a source for the T cells. For instance, assessments are performed from fresh blood samples of 0.5 cc to 60 cc, depending on the expected frequency of the virus-specific T cells being assessed. (Larger samples may be necessary from subjects with lymphocytopenia.)

In some variations, the sample is a fresh sample that has never been frozen. In some variations, the sample is cryopreserved under conditions that preserve the integrity of the immune cells therein. This may include preservation using dimethylsulfoxide-containing media (e.g., 5-10% solutions) or other solutions designed to maximize the viability of healthy human mononuclear cells during cryopreservation, to enable their subsequent thawing for functional analyses.

Biological Sample Preparation and Stimulation

Red blood cells are unnecessary for the analysis described herein.

In some variations, white cells are separated from red cells, e.g., by ficoll gradient centrifugation, prior to antigen stimulation.

In some variations, red cells are lysed prior to antigen stimulation.

Between sample collection and biological marker / phenotype analysis, the T cells are stimulated with antigen from at least one virus of interest.

In some variations, inactive virus is used to stimulate the T cells. In some variations, whole viral protein is used as antigen to stimulate the T cells. In some variations, peptides from viral proteins are used as antigens to stimulate the T cells. In some variations, the antigen is an isolated antigen preparation (e.g., isolated peptides or proteins). In some variations, a virus like particle (VLP) or other expedient known in the art for antigen stimulation is used to present the antigen to the immune cells in the sample.

In some variations, PBMC from the sample are incubated with the antigen. Antigen processing and antigen presenting immune cells present in the PBMC facilitate presentation of the antigen to T cells and T cell stimulation. In some variations, antigens are pre-processed into peptides and optionally formulated with MHC molecules, in which case stimulation of isolated T cells from the sample is possible.

Any protein or peptide recognized by immune cells can be used in the stimulation protocol. Many of the viruses of interest herein are well known and characterized, and peptides suitable for antigens are commercially available. (See, e.g., https://www.jpt.com/products/pepmix-peptide-pools/)

By way of example, if the latent virus of interest is CMV, suitable antigens for T cell stimulation include CMV tegument phosphoprotein 65 (pp65), or CMV immediate early 1 (1E1) protein, or one or more antigenic fragments of either of these proteins, or mixtures of these proteins or antigenic fragments.

If the latent virus of interest is EBV, exemplary antigens suitable for practice of the invention include EBNA1, EBNA2, LMP1, and LMP2, as well as antigenic fragments thereof and mixtures thereof. If the latent virus of interest is HHV6, exemplary antigens include U54, U90, antigenic fragments thereof, and mixtures thereof. If the latent virus of interest is VZV, exemplary antigens include 1E62, fragments thereof, and mixtures thereof.

The antigen stimulation is performed for, e.g., a period of about 4-16 hours. Exemplary antigen stimulation periods of 5, 6, 7, 8, 9, 10, 11, 12, 13, 14, 15, 16 hours, or integer ranges defined by any of these numbers, is contemplated.

In some variations, a co-stimulatory molecule is used to stimulate the T cells contemporaneously or simultaneously with the viral antigen. Co-stimulation with anti-CD49d and/or anti-CD28 antibodies is specifically contemplated.

In some variations, a super-antigen, such as a bacterial super-antigen is used to stimulate an aliquot of the sample, to serve as a positive control.

Biological Markers

The evaluation of risk for viral reactivation comprises identification and quantification of subclasses of T cells from the antigen-stimulated sample. The subclasses are identifiable by biological markers expressed by the cells.

In some variations, the biological markers to be evaluated are protein markers. In some variations, the markers are mRNA's expressed in the cells that encode the protein markers.

Generally speaking, a marker-specific detection agent is used to detect each marker of interest. For mRNA's, oligonucleotide probes can be used for detection. For proteins, antibodies are exemplary marker-specific agents. For antibody detection, both polyclonal and monoclonal antibodies are suitable, with monoclonal providing a more consistent or reproducible result. Antigen binding fragments of antibodies are equivalent to whole antibodies for the purposes described herein. Marker-specific agents that comprise a detectable label are specifically contemplated.

Cytokine Markers

As described herein the four cytokines interleukin-2 (IL-2), interferon gamma (IFNγ), tumor necrosis factor alpha (TNFα), and macrophage inflammatory protein 1β (MIP-1β) can be used to identify and quantify T cell populations that are informative of a subject's risk for viral reactivation.

An exemplary sequence for human IL-2 (also known as T cell growth factor or TCGF) is set forth in the public UniProt database as entry UniProtKB—P60568 (IL2_HUMAN) (SEQ ID NO: 1):

```
MYRMQLLSCI ALSLALVTNS APTSSSTKKT QLQLEHLLLD

LQMILNGINN YKNPKLTRML TFKFYMPKKA TELKHLQCLE

EELKPLEEVL NLAQSKNFHL RPRDLISNIN VIVLELKGSE

TTFMCEYADE TATIVEFLNR WITFCQSIIS TLT
```

An exemplary seqeunce for human IFNγ is set forth in the public UniProt database as entry UniProtKB—P01579 (IFNG_HUMAN) (SEQ ID NO: 2):

```
MKYTSYILAF QLCIVLGSLG CYCQDPYVKE AENLKKYFNA

GHSDVADNGT LFLCILKNWK EESDRKIMQS QIVSFYFKLF

KNFKDDQSIQ KSVETIKEDM NVKFFNSNKK KRDDFEKLTN

YSVTDLNVQR KAIHELIQVM AELSPAAKTG KRKRSQMLFR

GRRASQ
```

An exemplary sequence for human TNFα (also known as TNF or cachectin) is set forth in the public UniProt database as entry UniProtKB—P01375 (TNFA_HUMAN) (SEQ ID NO:3):

```
MSTESMIRDV ELAEEALPKK IGGPQGSRRC LFLSLFSFLI

VAGATTLFCL LHFGVIGPQR EEFPRDLSLI SPLAQAVRSS

SRTPSDKPVA HVVANPQAEG QLQWLNRRAN ALLANGVELR

DNQLVVPSEG LYLIYSQVLF KGQGCPSTHV LLTHTISRIA

VSYQTKVNLL SAIKSPCQRE TPEGAEAKPW YEPIYLGGVF

QLEKGDRLSA EINRPDYLDF AESGQVYFGI IAL
```

An exemplary sequence for human MIP-1β (also known as CCL4) is set forth in the public UniProt database as entry UniProtKB—P13236 (CCL4_HUMAN) (SEQ ID NO: 4):

```
MKLCVTVLSL LMLVAAFCSP ALSAPMGSDP PTACCFSYTA

RKLPRNFVVD YYETSSLCSQ PAVVFQTKRS KQVCADPSES

WVQEYVYDLE IN
```

Antibodies for detecting each of these cytokine markers are commercially available. To facilitate detection, labeled antibodies are contemplated. To facilitate multiplex detection, antibodies with different detectable labels for each cytokine are contemplated.

The specific markers described herein are not contemplated as the exclusive or only markers suitable for identifying the informative T cell populations of interest. The use of a single surrogate marker, or different combinations of markers that behave as a surrogate, are contemplated as alternative tools for identifying the T cell populations described herein. The power of a surrogate marker or marker set can be evaluated by the statistical correlation between the surrogate's expression and the expression of the marker phenotypes described herein. The power of the surrogate(s) to predict viral reactivation risk is confirmable by a population study as described herein using IL-2, IFNγ, TNFα, and MIP-1β.

Surrogates can be identified by comparing expression patterns between the markers described herein and the candidate surrogate marker(s). Alternatively, surrogates are identified by studying the expression pattern of markers in the informative T cell subpopulations identified herein, to identify other marker signatures that serve to identify the T cell subpopulations.

In some variations of the invention, identification of T cells that express cytokine markers is achieved by intracellular detection of the markers. For example, in some variations, after antigen stimulation, the T cells are fixed using standard techniques and permeabilized to antibodies, to facilitate intracellular detection of the cytokine markers of interest.

In other variations, other multiplex technologies (e.g., mass cytometry or visual imaging-based detection technologies are used to identify individual cells that co-express combinations of cytokines following stimulation with target viral antigens leading to functional activation). Single Cell RNA-sequencing to identify these expression signatures also is contemplated.

T Cell Markers and Controls

Additional markers can be utilized to identify or select or distinguish T cells (e.g., to exclude from analysis other cells). In some variations, these markers include, but are not limited to, CD4, CD8, CD14, CD16, CD19, and CD56.

The marker CD3 (T-cell surface glycoprotein CD3 epsilon, UniProtKB—P07766 (CD3E_HUMAN)) is useful to identify T cells.

The marker CD4 (T-cell surface glycoprotein CD4, UniProtKB—P01730 (CD4_HUMAN)) is useful to identify CD4+ T cell subset of CD3+ T cells.

The marker CD8 (T-cell surface glycoprotein CD8 alpha chain, UniProtKB—P01732 (CD8A_HUMAN); or T-cell surface glycoprotein CD8 beta chain, UniProtKB—P10966 (CD8B_HUMAN)) is useful to identify CD8+ T cell subset of CD3+ T cells.

The marker CD14 (Monocyte differentiation antigen CD14; UniProtKB—P08571 (CD14_HUMAN)) is useful to exclude monoctyes from the T cell analysis.

The marker CD16 (Low affinity immunoglobulin gamma Fc region receptor III-A, UniProtKB—P08637 (FCG3A_HUMAN)) is useful to exclude natural killer cells from analysis.

The marker CD19 (B-lymphocyte antigen CD19, UniProtKB—P15391 (CD19_HUMAN)) is useful to exclude B cells from analysis of the T cells of interest.

The marker CD20 (B-lymphocyte antigen CD20, UniProtKB—P11836 (CD20_HUMAN)) is useful to exclude B cells from analysis of the T cells of interest.

The marker CD56 (Neural cell adhesion molecule 1, UniProtKB—P13591 (NCAM1_HUMAN)) is useful to exclude natural killer cells from the T cell analysis.

Staining for free amino or other markers of dead cells is useful (indicated, for example, by positive staining for free amine labeling dye (LIVE/DEAD® Aqua) to exclude such cells from analysis.

Cell Sorting—Phenotype Differentiation—Quantitative Detection

After antigen stimulation, T cells of informative phenotype(s) are quantified. In some variations, an absolute quantity is determined. In some variations, a relative quantity is determined. Relative quantity is expressed relative to a suitable denominator. For instance, T cells of a phenotype of interest can be expressed as a total percentage of CD8+ T cells, or a total percentage of T cells.

In some variations, cells are sorted by phenotype and quantified using automated or semi-automated techniques. Suitable techniques include flow cytometry, mass cytometry, imaging cytometry, or slide scanning cytometry. Singe cell RNA sequencing or PCR also are contemplated.

A preferred technique for T cell analysis is multiparameter flow cytometry, a technique that permits rapid measurement of multiple characteristics of individual cells as they flow past laser/light in a focused fluid stream. See, e.g., O'Donnell et al., "Multiparameter Flow Cytometry: Advance in High Resolution Analysis," *Immune Network*, 13(2): 43-54 (2013), incorporated herein by reference in its entirety.

Using flow cytometry, it is possible to distinguish CD8+ T cells of interest from other T cells or non-T cells; and to measure cytokine markers of interest (e.g., IL-2, IFNγ, TNFα, and MIP-1β). By measuring each parameter, it is possible to sort and quantify the CD8+ T cells by each cytokine phenotype represented by the measured cytokines. For example, with cytokines IL-2, IFNγ, TNFα, and MIP-1β, it is possible to sort the T cells into the sixteen phenotypes based on whether the cell is scored as expressing, or not expressing, a particular cytokine ($2^4$=16 phenotypes).

As described below in greater detail, T cells that are CD8-positive (CD8+), IL-2-positive (IL-2+), IFNγ-positive (IFNγ+), TNFα-positive (INFα+), and MIP-1β-positive (MIP-1β+) are an informative phenotype insofar as increased quantities of these cells correlates with decreased CMV viral reactivation in hematopoietic cell transplant patients. Thus, greater numbers of these cells correlate with a subpopulation of subjects that appear to be more resistant ("protected", "PHENOTYPE-P") from viral reactivation. Quantifying PHENOTYPE-P T cells is specifically contemplated. When assessed alone, an increased percentage of Phenotype-P T cells in the sample from the subject is correlated with a decreased risk of viral reactivation in the subject, and decreased percentage of Phenotype-P T cells in the sample is correlated with an increased risk of viral reactivation in the subject.

T cells that are CD8-positive (CD8+), IL-2-negative (IL-2−), IFNγ-positive (IFNγ+), TNFα-negative (TNFα−), MIP-1β-positive (MIP-1β+) are an informative phenotype insofar as increased quantities of these cells correlated with increased frequency of CMV viral reactivation in hematopoietic cell transplant patients. Thus, greater numbers of these cells correlate with a subpopulation of subjects that appear to be more susceptible ("non-protected", "PHENOTYPE-N") from viral reactivation. Quantifying PHENOTYPE-N T cells is specifically contemplated. When assessed alone, an increased percentage of Phenotype-N T cells in the sample from the subject is correlated with an increased risk of viral reactivation in the subject, and a decreased percentage of Phenotype-N T cells in the sample are correlated with a decreased risk of viral reactivation in the subject.

Phenotypes N and T can be evaluated together to give a still more powerful risk assessment. The combination of a high percentage of Phenotype-P T cells and a low percentage of Phenotype-N T cells in the sample is correlated with a low risk of viral reactivation in the subject. The combination of a high percentage of Phenotype-N T cells and a low percentage of Phenotype-P T cells in the sample is correlated with high risk of viral reactivation in the subject.

Suitable flow cytometer detector settings are established using standard beads to optimize the instrument (cytometer setup and tracking beads, BD catalog #642412). Single-stained samples for each reagent are acquired, and if necessary, voltages on each detector are lowered to ensure that the brightest stained cells are still on scale (not in the highest channel on the histogram). Once these settings are established they are not adjusted again. Single-stained controls for each reagent are then acquired and saved during each run to establish spillover coefficients, which are calculated automatically by BD FACS DIVA software, for example. (Software determination by other FACS analysis, such as FLOWJO software, could also be used.)

For intracellular markers such as the cytokines/chemokine assessed here, antibody capture compensation beads (instead of cells, BD catalog #552843) are used for single-stained controls. Because the beads are small and fixed, and permeablized cells are also smaller than unpermeablized cells, it is important that the detection threshold is set low enough to include all cells in the well.

Interpretation of T Cell Phenotype Data

Figure 16:
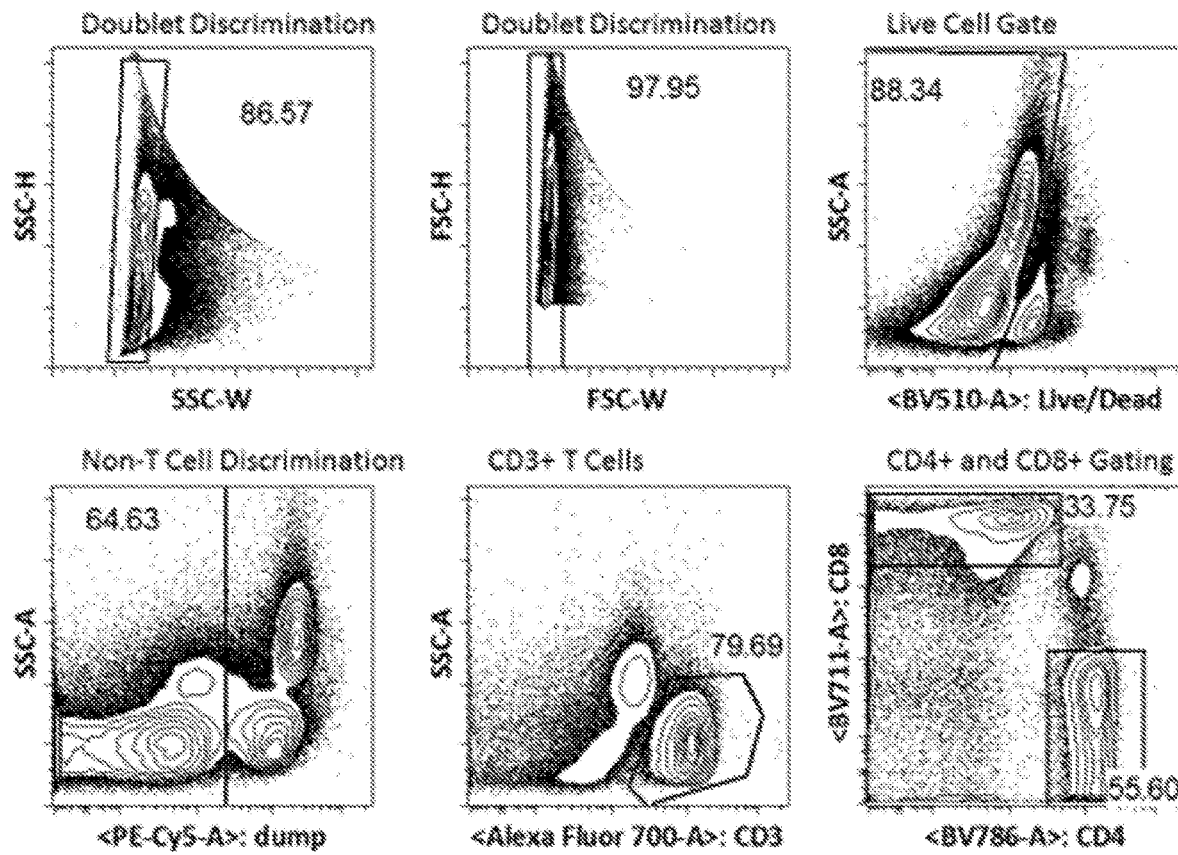
FIG. 16 depicts exemplary flow cytometry density plots demonstrating the gating strategy to identify CMV-responsive CD4+ and CD8+ T cells.

Exemplary flow cytometry data acquisition and gating selection is as follows: doublets are excluded using pulse-processing technique (ssc-width vs ssc area, fsc-width vs fsc area—larger width signal than cluster of majority of cells indicates aggregation of cells which are excluded). Dead cells (indicated by positive staining for free amine labeling dye (live-dead aqua) are excluded, followed by exclusion of non-T cells ('dump' channel-CD14/CD16/CD19/CD56+ cells). These exclusion settings are followed by positive gating of CD3+ cells. The CD3+ cells are selected/gated as single+ CD4 and CD8 gates. Exemplary gating is depicted in FIG. 16

Figure 17:
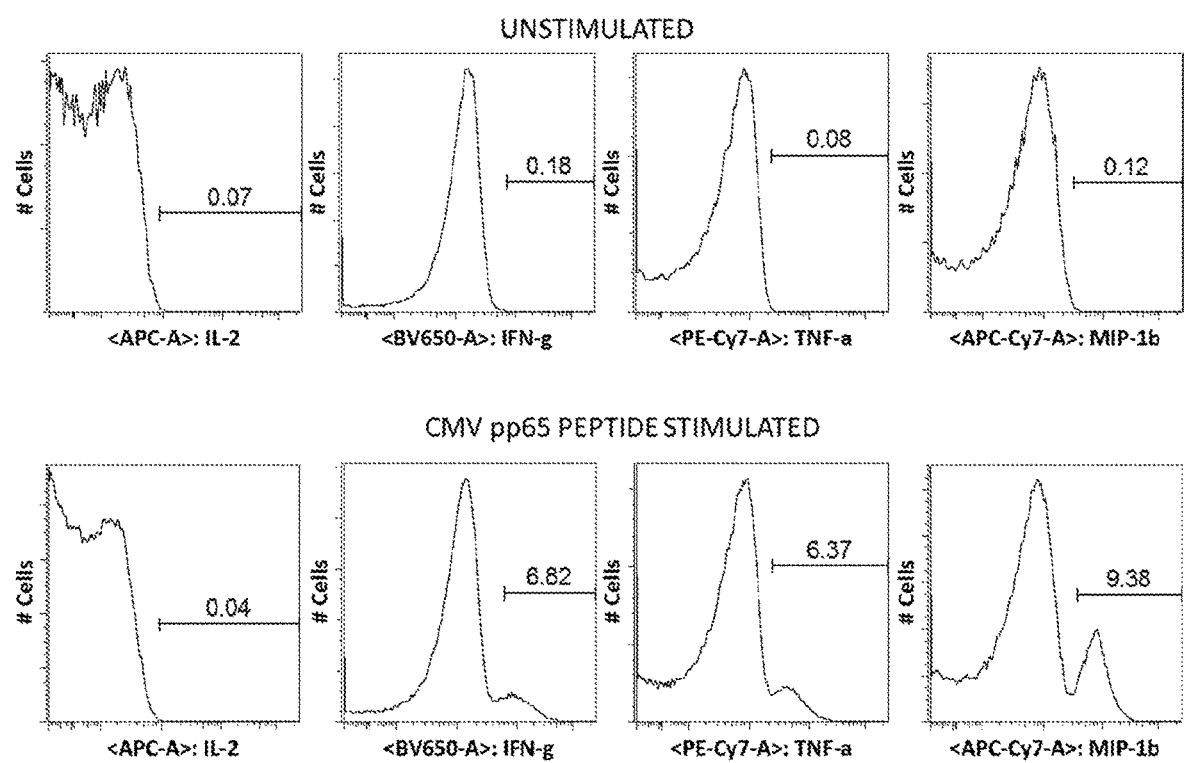
FIG. 17 depicts exemplary histograms showing CD8+ T cell expression of indicated cytokines and chemokines in response to stimulation with CMV peptides, useful for gating strategy to define cytokine subsets.
Figure 18A:
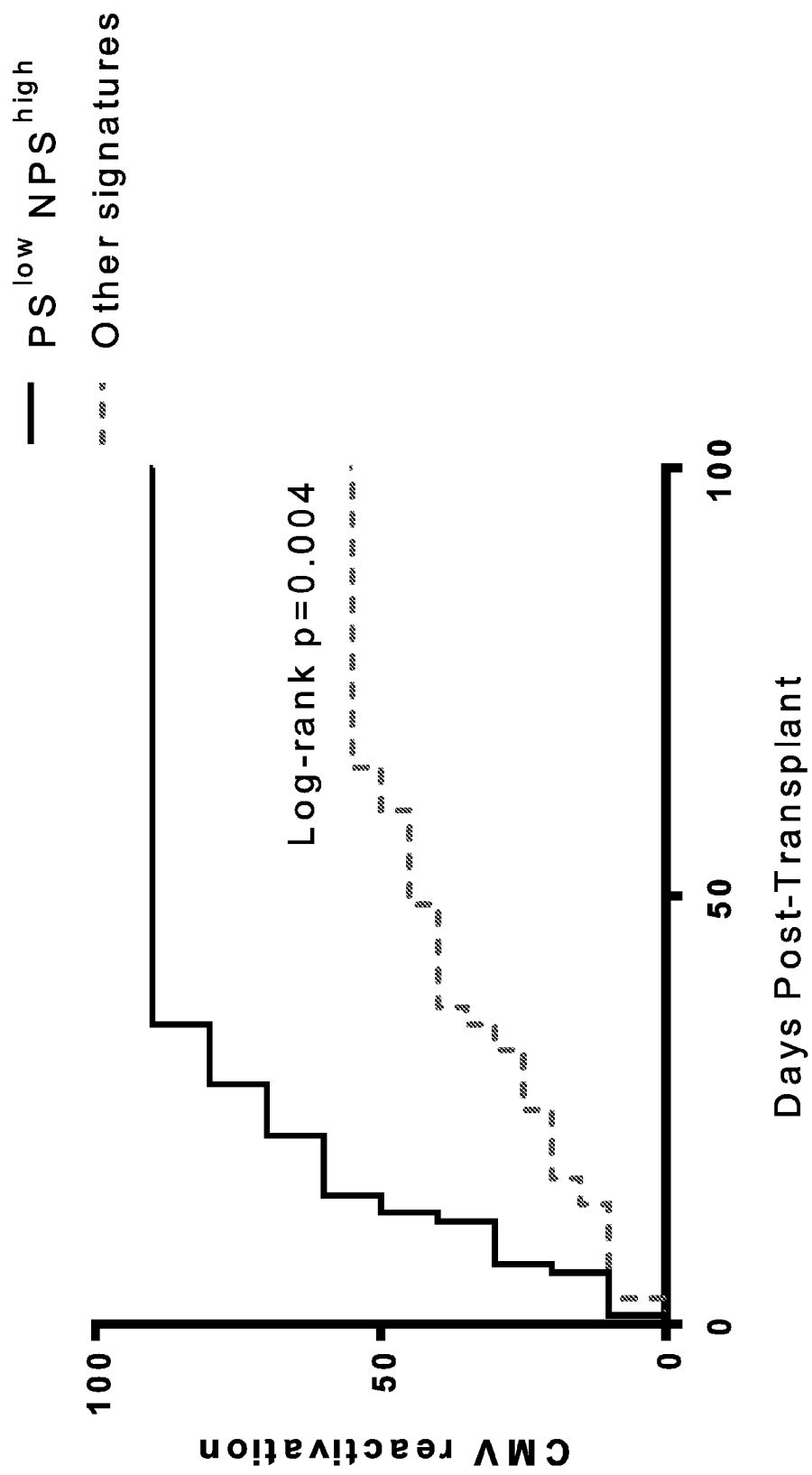
FIG. 18A is a graph depicting cumulative incidence of CMV reactivation over time (percentage of hematopoietic cell transplant subjects) stratified based on whether the subject has a low percentage of T cell PS phenotype in combination with a high percentage of T cells with an NPS phenotype, versus any other PS/NPS signature.
Figure 18B:
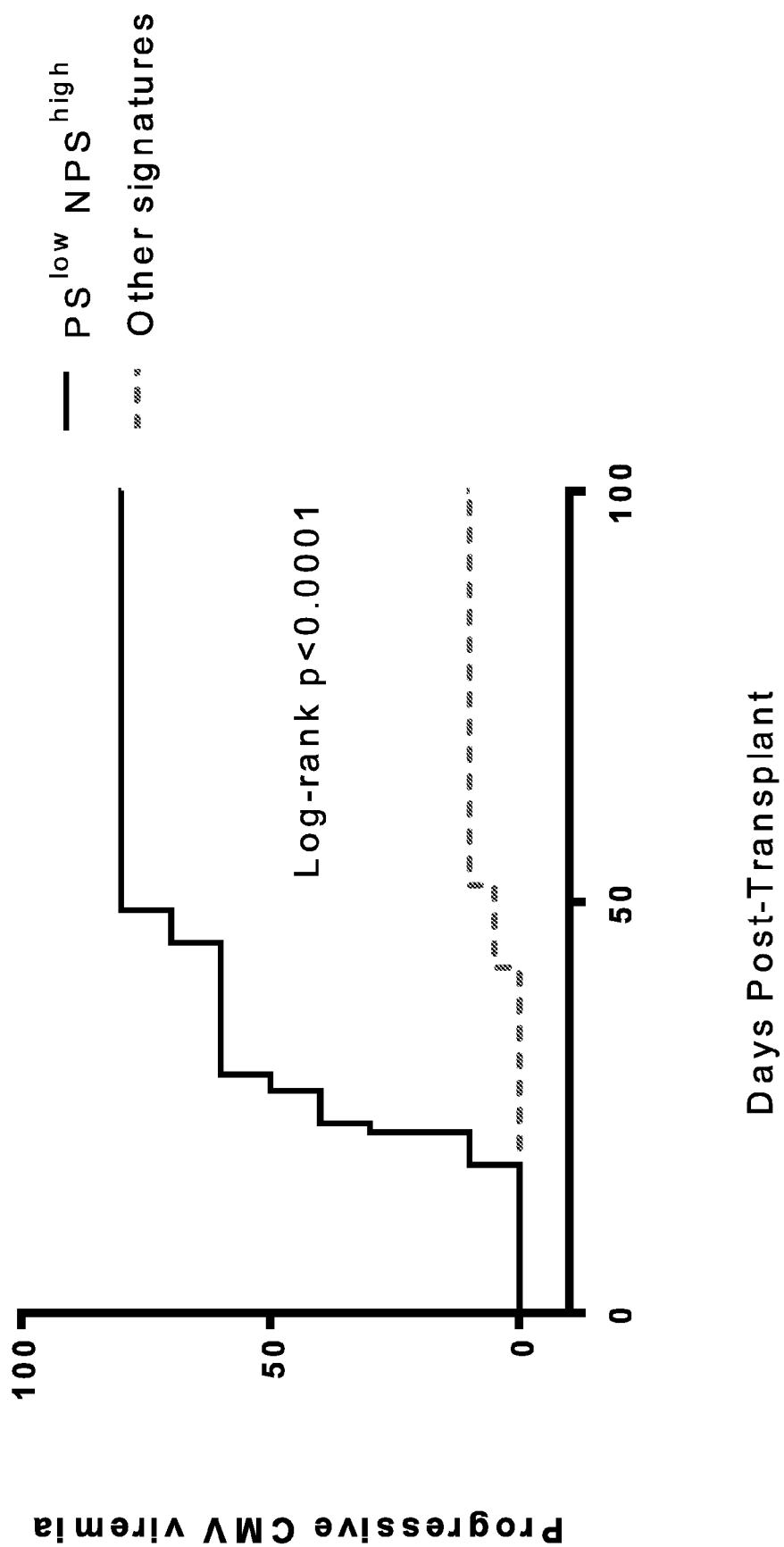
FIGS. 18B-18C are graphs depicting cumulative incidence of progressive CMV viremia over time (percentage of hematopoietic cell transplant subjects) stratified based on whether the subject has a low percentage of T cell PS phenotype in combination with a high percentage of T cells with an NPS phenotype, versus any other PS/NPS signature. Progressive CMV viremia was defined as CMV reactivation with peak viral load >1000 IU/mL that required initiation of pre-emptive antiviral therapy.
Figure 18C:
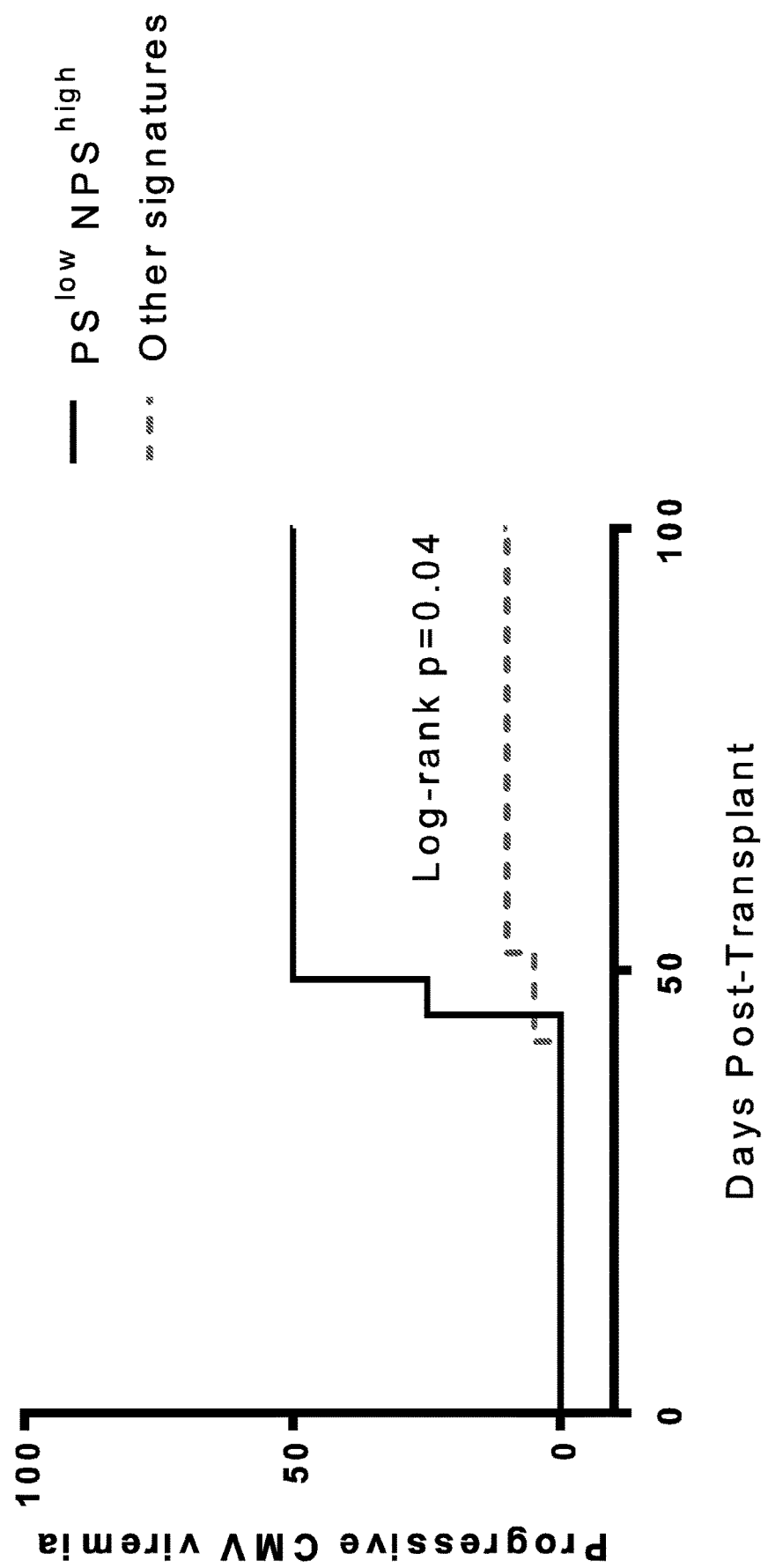
Figure 18D:
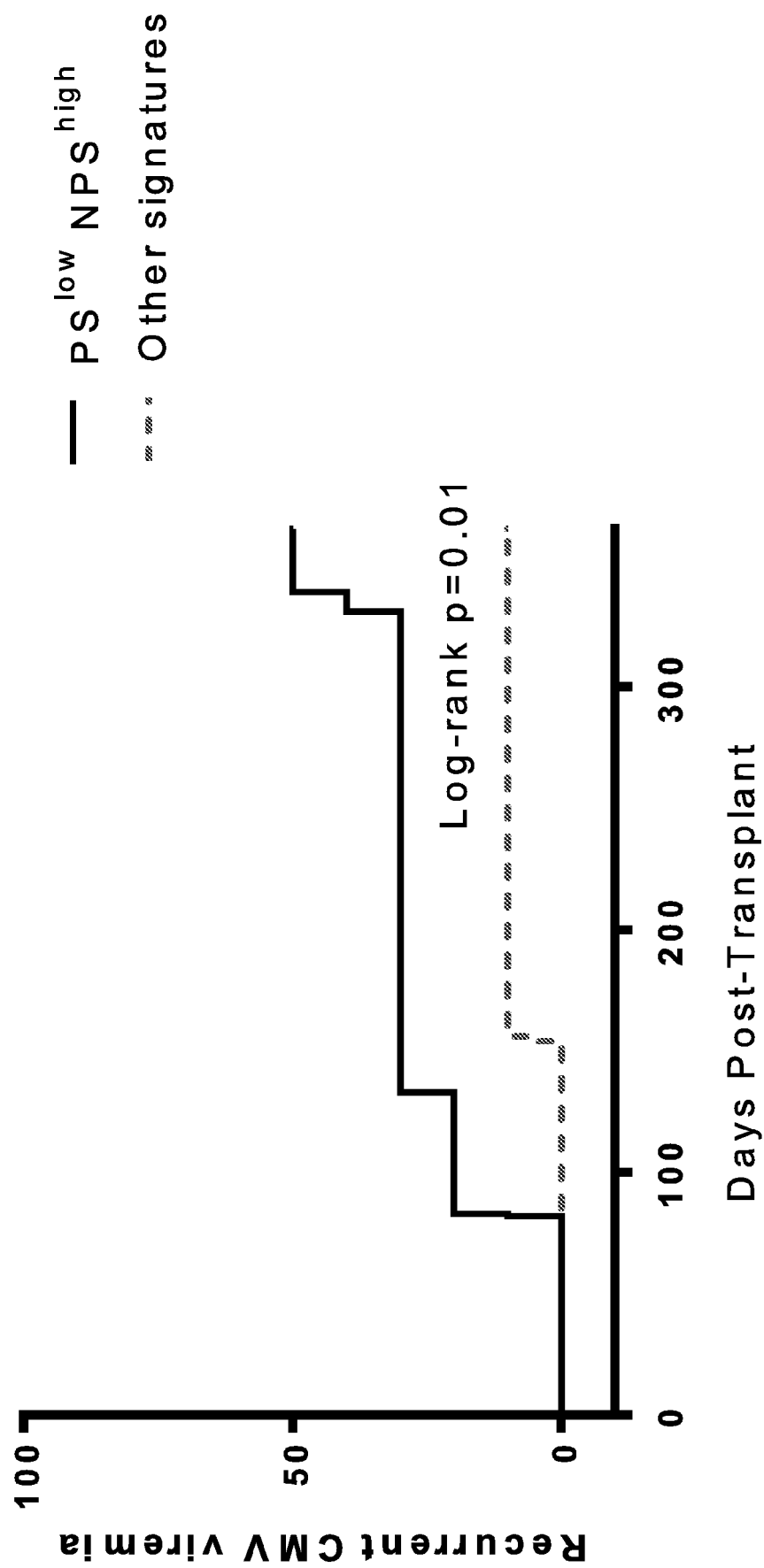
FIG. 18D is a graph depicting cumulative incidence of recurrent CMV viremia over time (percentage of hematopoietic cell transplant subjects) stratified based on whether the subject has a low percentage of T cell PS phenotype in combination with a high percentage of T cells with an NPS phenotype, versus any other PS/NPS signature. Patients with the event are those who had a second of viremia after achieving spontaneous or treatment induced clearance of initial viremia. In other words, patients who had 2 separate episodes of viremia.

The cytokine/chemokine gate is set by taking an un-stimulated control sample and looking at CD4+ or CD8+ histograms. (Exemplary data for CMV-stimulated cells is depicted in FIG. 17) A positive gate is set by placing the gate to the right edge of the histogram, such that the + signal in the region is less than 0.2%. (Note that it can be much lower than this, depending on the amount of background cytokine/chemokine signal is in the control sample, but the target is <0.2%.) Once the gates are drawn, the positive events are detected and the cytokine signature is determined by combination Boolean gating in FLOWJO® software (Flowjo LLC, Tel. +1-541-201-0022; techsupport@flowjo.com).

In some variations, raw numbers of cells of phenotype(s) of interest are used for risk assessment/stratification (e.g., an un-normalized percentage of CD8+ cells with a phenotype of interest). In some variations, an absolute number of cells having phenotype(s) of interest are used for risk assessment/stratification. Absolute numbers for a subject in the peripheral blood are calculated by multiplying the percentage of CD8+ cells possessing each chemokine phenotype of interest by the absolute number of CD8 cells (e.g., cells per microliter) in the subject.

Figure 3:
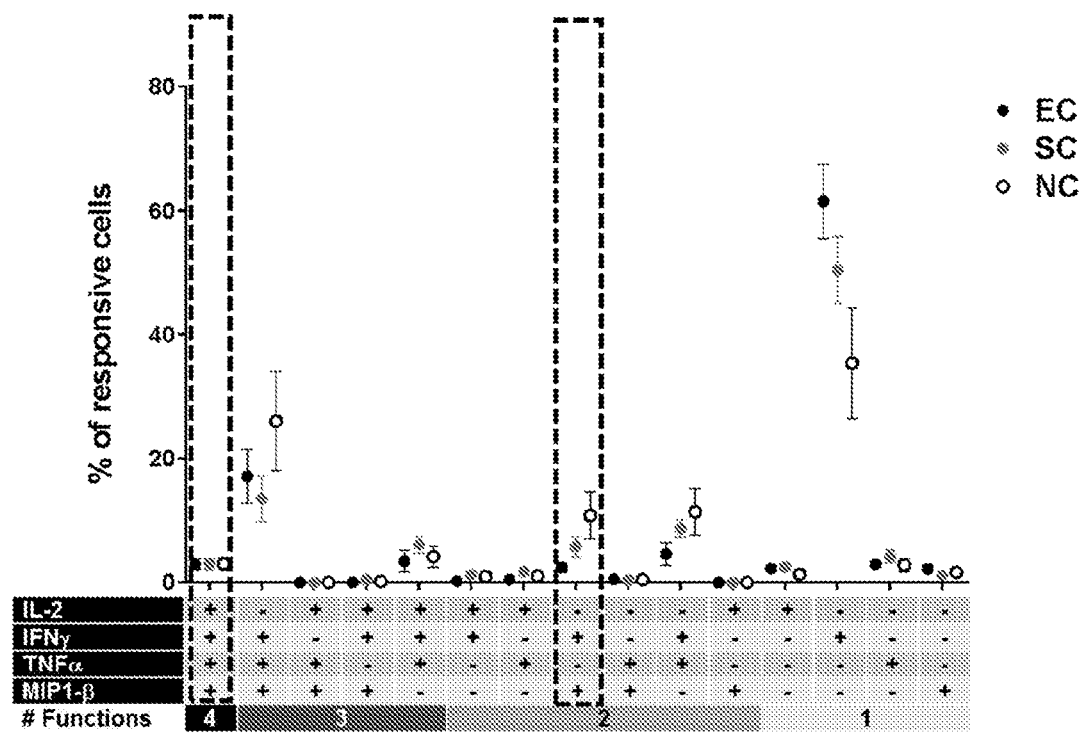
FIG. 3 depicts the functional signatures of fifteen (15) possible combinations for CD4+ (Top) and CD8+ (Bottom) CMV responsive T cells, grouped by CMV outcome.
Figure 3:
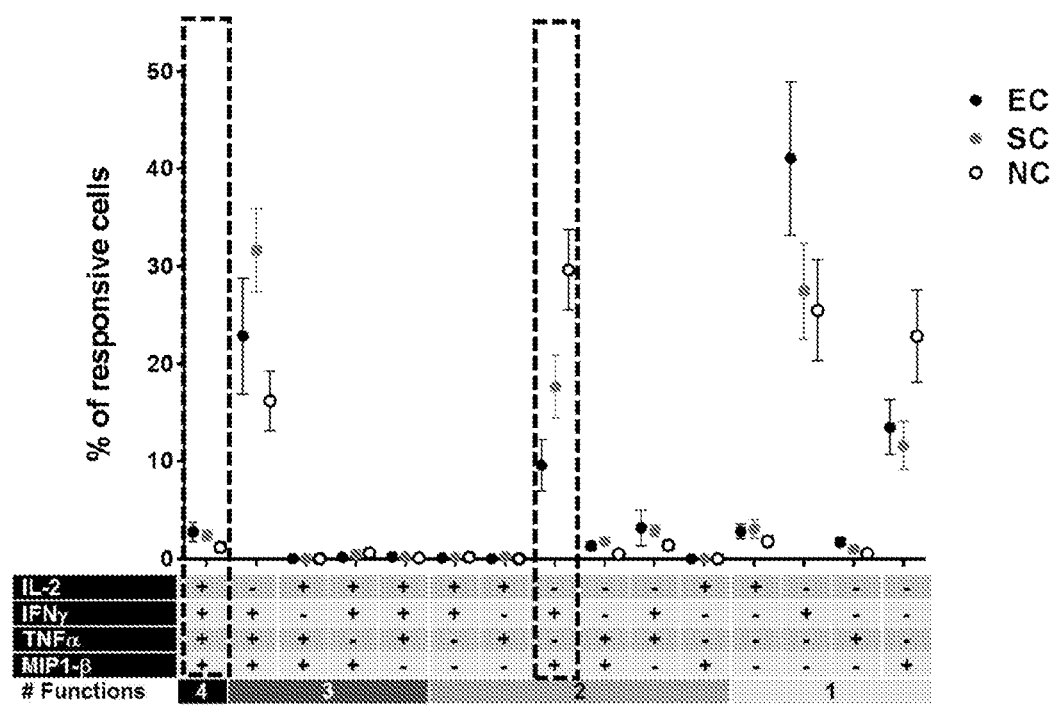
Figure 4:
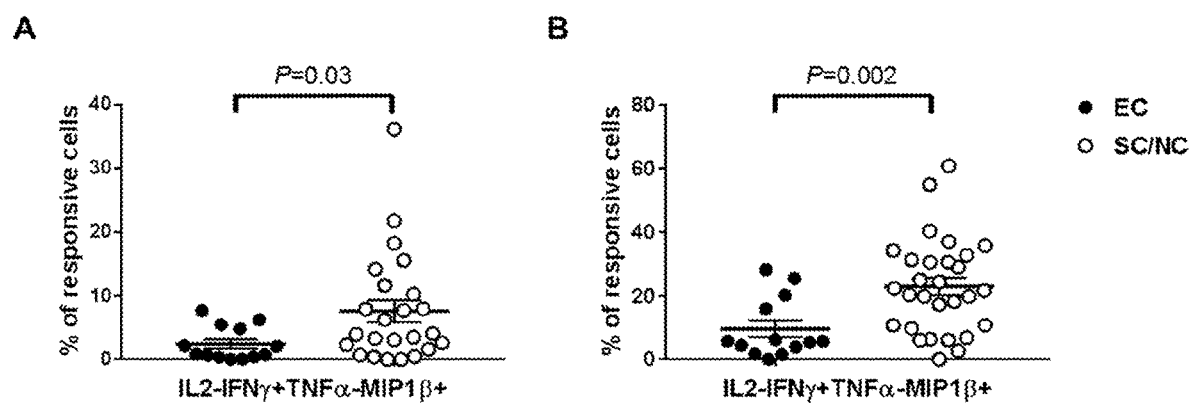
FIGS. 4A and 4B depict scatter plots of the non-protective (NPS) functional signature of CD4+ (FIG. 4A) and CD8+ (FIG. 4B) T cells grouped by CMV outcome.
Figure 5:
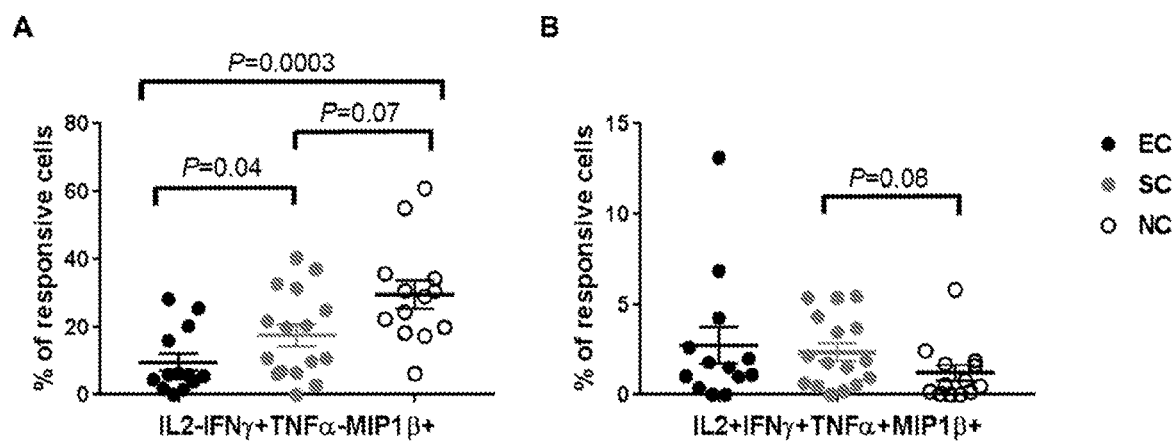
FIGS. 5A and 5B depict scatter plots of the non-protective (NPS.
Figure 6:
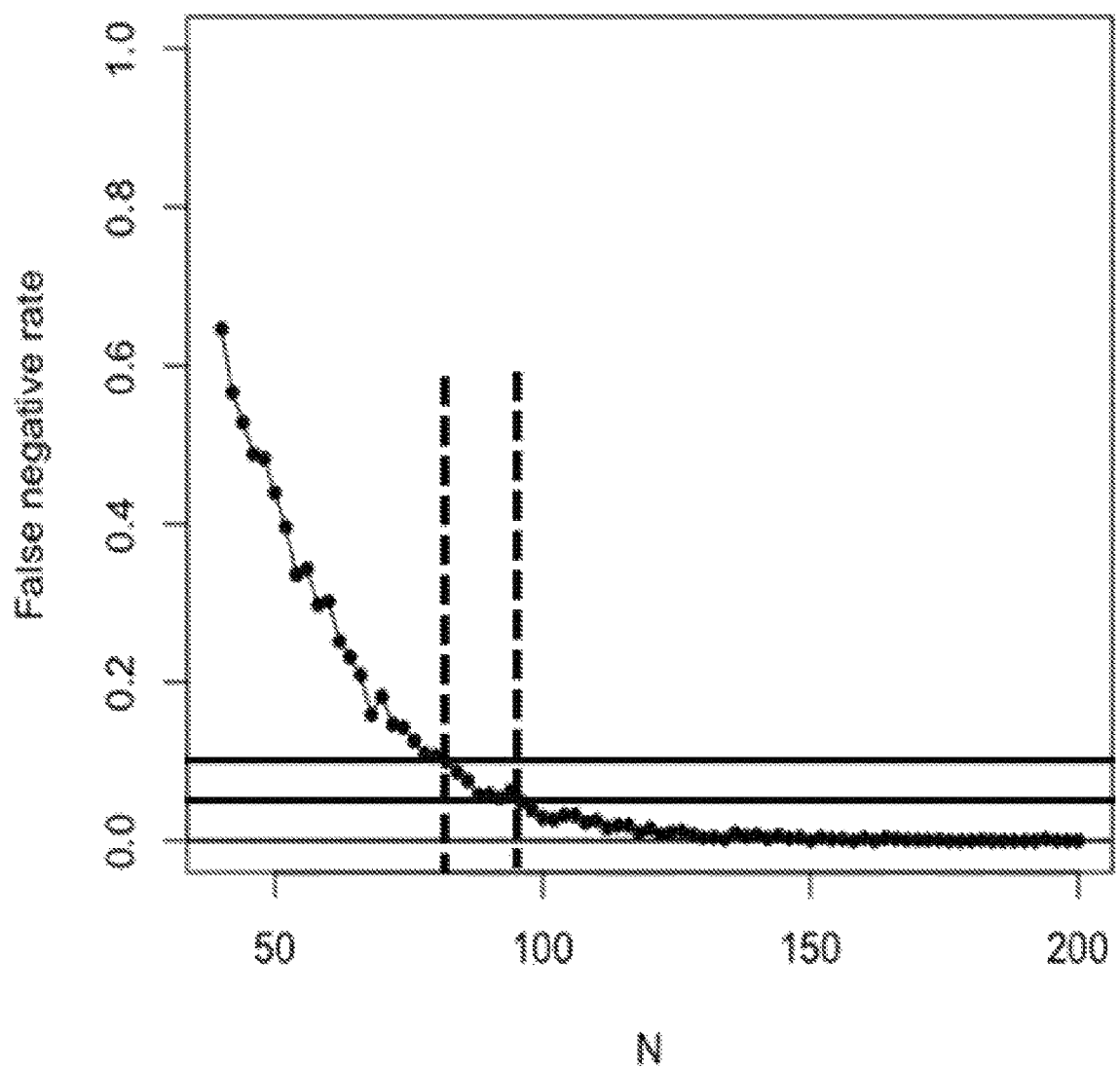
FIG. 6 depicts a Monte Carlo simulation to determine the minimum number of events required to have a reliable measurement of fifteen (15) functional signatures. As indicated by the dotted lines, at least 82 and 96 events are needed for 10% and 5% error rates in black bold lines, respectively. Based on this we censored patient samples with <96 events in the CMV-responsive cell gate in functional signature analysis.

In some variations, percentages of phenotypes of interest are calculated as a fraction/percentage of the number of responsive cells in the assay. For example, with the four-cytokine assay, there are sixteen possible phenotypes based on whether cells are scored as positive for each cytokine ($2^4$=16 phenotypes). Of these sixteen phenotypes, fifteen are scored as responsive (and the −/−/−/− quadruple negative cells are ignored). An exemplary histogram for CMV pp65 peptide-stimulated CD8+ T cells is depicted in FIG. 3. Cells with a phenotype of interest are calculated as a percentage of the total of the fifteen responsive phenotypes. (With such a calculation, the fifteen responsive phenotypes total 100%).

Standard statistical modeling can be used to adjust the sensitivity and specificity with which the phenotypes described herein will predict risk of viral reactivation. For instance, receiver operating characteristic curves can be established for particular decision thresholds. Classification And Regression Tree (CART) analysis, mathematical modeling, and machine learning to optimize weighting of each informative phenotype is specifically contemplated.

In an initial dataset described below, simple defined cutoffs (e.g., >10% PHENOTYPE-N cells within the parent CD8+ gate and <2% of the PHENOTYPE-P cells within the parent CD8+ gate, using the percentage of responsive cells approach described above) can be used to get significant discrimination of patients that suffered viral reactivation and patients that did not, as discussed below in greater detail. These are only exemplary cutoffs and can be further optimized with larger datasets and standard statistical modeling.

Differences in the expression of cytokine profiling across groups were determined by using the Fisher Exact Test and Wilcoxon Mann—Whitney U-Test where appropriate. Log-rank test was used to assess differences in time-to-event. Statistical analyses were performed using prism (Graphpad Software, Inc).

Adjusted Monitoring of Subjects Identified as Having Stratified Risk

It is possible to screen blood or plasma samples from immune-compromised subjects for viral load, to provide a diagnosis of developing infection. See, e.g., Kraft et al., "Interpreting Quantitative Cytomegalovirus DNA Testing: Understanding the Laboratory Perspective." *Clinical Infections Diseases,* 54(12) 1793-97 (2012). Indeed, such screening for CMV is standard of care for transplant patients, including hematopoietic cell transplant patients, but it is not without inconvenience and cost. The frequency of monitoring currently varies significantly between medical centers/practices.

The analytical techniques described herein permit modulation of the frequency of viral load testing. For example, a subject determined to have lower risk of viral reactivation can be tested less frequently for viral load; a subject determined to have greater risk for viral reactivation according to the methods described here can be tested more frequently for viral load, to permit earlier detection of viral load increases or trends in increasing. For example, standards of practice at some facilities typically involve periodic monitoring of CMV viral load one to three times weekly in the first 60-100 days following HCT. In one potential application of this invention, patients determined to have higher-risk (based on the assessment of Phenotype-P and/or Phenotype-N cells, preferably together in a combined algorithm) continue to be monitored frequently; those at low risk might safely be monitored less frequently (e.g. once per 8, 9, 10, 11, 12, 13, 14, 15, 16, 17, 18, 19, 20, 21, 22, 23, 24, 25, 26, 27, 28, 29, 30, or 31 days) decreasing costs and inconvenience of testing.

The combination of viral load testing and risk assessment can together be used to modulate therapeutic intervention. For example, antiviral therapy is initiated more quickly in a subject determined to be at higher risk for viral reactivation according to the T cell analysis methods described herein. For instance, therapy might be initiated at a lower absolute viral load measurement or more quickly upon detection of an upward trend in viral load measurements for subject stratified in a high risk group based on Phenotype P and/or Phenotype N measurements.

Prophylaxis of Subject Identified as Having Elevated Risk

Anti-viral therapeutic agents exist, but use of these agents for prophylaxis is not currently standard-of-care for all immune-compromised subjects. The drugs are expensive and prophylaxis exposes patients who are potentially in a low risk group to serious side effects, including nephrotoxicity (e.g., for agents such as Foscarnet) or myelosuppression (e.g., for agents such as ganciclovir or valganciclovir). However, when sufficiently high risk patients can be identified, as the data herein indicates, the rational basis for pre-emptive therapy becomes more compelling.

In some variations, the invention further comprises administering, to a subject identified as having high risk of viral reactivation according to the techniques described herein, a prophylaxis that comprises an antiviral chemotherapeutic agent or an antiviral cellular therapy. In some embodiments, a healthcare provider performs or controls the risk assessment and the therapeutic/prohylaxis decision. In some variations, a healthcare provider controls only the therapy/prophylaxis, based on receipt of the results of a risk assessment as described herein.

Exemplary antiviral chemotherapeutic agents are listed in the following table. In some variations, the prophylactic course of treatment is the same dose and duration as the therapeutic course of treatment. In some variations, prophylaxis is continued until the immune-compromised condition is alleviated. For example, for a subject that has received a hematopoietic cell transplant or cytotoxic chemotherapy, prophylaxis is continued until white blood cell counts improve.

cells); polyclonal T cell lines (made by culturing cells in the presence of the target antigen with co-stimulation to enrich and expand the pathogen-specific T cell population to high numbers). Companies with CAR-T, polyclonal T cell line, and transgenic T cells in the pipeline include Kite Pharmaceutical, Juno Therapeutics, Novartis, Ziopharm, Atara, Maxcyte, Autolus, Celgene, Bluebird, Pfizer, CRISPR Therapeutics, Cell Medica, and others.

For example, for subjects determined to be at elevated risk for CMV, prophylaxis with CMV-specific cytotoxic T lymphocytes is contemplated. See, e.g., Bao et al., "Adoptive immunotherapy with CMV-specific cytotoxic T lymphocytes for stem cell transplant patients with refractory CMV infections," J. Immunother. (2012) 35(3): 293-98, incorporated herein by reference. Such cells are being developed by Atara Biotherapeutics. See also international patent application no. PCT/US2014/062698 (published as WO2015066057), directed to expansion of cmv-specific t cells from cmv-seronegative donors, incorporated herein by reference. Zostavax® vaccine (Merck) is contemplated as prophylaxis for zoster.

The materials and methods described herein also are useful for identifying the most suitable candidates for receipt of investigative or approved antiviral vaccine compositions.

| Brand name (Generic name) | Manufacturer | Chemical name | Chemical structure | Mechanism of action | Comments |
|---|---|---|---|---|---|
| Ganciclovir (Cytovene-IV) | Roche | 9-[[2-hydroxy-1-(hydroxymethyl)-ethoxy]methyl]guanine. | $C_9H_{13}N_5O_4$ | Inhibition of DNA polymerase (pUL54) | Activity dependent on phosphorylation by pUL97 kinase |
| Valganciclovir (Valcyte) | Genentech (Roche) | L-Valine, 2-[(2-amino-1,6-dihydro-6-oxo-9Hpurin-9-yl)methoxy]-3-hydroxypropyl ester, monohydrochloride. | $C_{14}H_{22}N_6O_5$ | Inhibition of DNA polymerase (pUL54) | Currently the drug of choice to treat CMV infections |
| Foscarnet (Foscavir) | Pfizer | Trisodium phosphonoformate | $CH_3O_5P$ | Inhibition of DNA polymerase (pUL54) | |
| Cidofovir (Vistide) | Gilead | 1-[(S)-3-hydroxy-2-(phosphonomethoxy)propyl] cytosine dihydrate (HPMPC) | $C_8H_{14}N_3O_6P$ | Inhibition of DNA polymerase (pUL54) | |
| Maribavir | Shire | 5,6,-dichloro-2-isopropylamino-1-β-l-ribofuranosyl-1H-benzimidazole | $C_{15}H_{19}Cl_2N_3O_4$ | Competes with ATP for binding to pUL97. | After successful phase I and II trials, maribavir, at a potentially suboptimal selected dosage, failed to show efficacy in the prevention of CMV disease in a phase III trial |
| Brincidofovir (CMX001) | Chimerix | Phosphoric acid, [[(S)-2-(4-amino-2-oxo-1(2H)-pyrimidinyl)-1-(hydroxymethyl) ethoxy]methyl]mono[3-(hexadecyloxy)propyl] ester | $C_{27}H_{52}N_3O_7P$ | Inhibition of DNA polymerase (pUL54) | Oral lipid conjugate of cidofovir with braod antiviral activity against dsDNA viruses In the phase III trial, brincidofovir failed to prevent clinically significant CMV infection through week 24 after HCT |
| Letermovir | Merck | 3-(2-methoxy-5-(trifluoromethyl)phenyl)-4H-guinazolin-4-yl)acetic acid | $C_{29}H_{28}F_4N_4O_4$ | Inhibits CMV DNA synthesis at a late step by targeting the pUL56 subunit of the terminase enzyme complex | Most potent in vitro anti-CMV agent to date |

Suitable cellular therapies for prophylaxis include antiviral chimeric antigen receptor T cells (CART) cellular therapy; transgenic tcr-transduced t cells (TCR transgenic For example vaccines are being developed to reduce CMV reactivation. (See, e.g., The Lancet Haematology, Vol. 3, No. 2, e87-e98 (Dec. 23, 2015); and Chiuppesi et al., "Identification of a Continuous Neutralizing Epitope within UL128 of Human Cytomegalovirus," J.Virology, Accepted manuscript posted online 11 Jan. 2017, doi: 10.1128/JVI.01857-16, incorporated herein by reference.

Other risk factors that can be weighed for the decision to implement prophylaxis or pre-emptive antiviral therapy include evidence of T-cell depletion, use of unrelated donors for transplant, CMV seronegative versus seropositive status of donors, existence of active graft-vs-host disease, timing post-transplant (with risk being higher in first 100 days), lymphoid malignancy, lymphopenia (absolute lymphocyte count below 300), and CMV viral load.

The invention will be further understood from the examples which follow, which form part of the description of the invention.

EXAMPLE 1

The following exemplary protocol is suitable for T cell analysis described herein. The assay is described with respect to assessment for risk for CMV reactivation, but similar procedures can be used for other viruses. Variations and equivalents will be apparent to scientists in the field.

Specimens:
PBMC (either thawed from cryopreserved specimen or freshly prepared by ficoll centrifugation)
Plasticware:
15 ml conical tube (Falcon cat #352097)
96 well v-bottom plate (Nunc cat #249570)
Chemicals/Solutions:
RPMI media (Gibco cat #22400-089)
PBS (Corning cat #21-031-CV)
Fetal Bovine Serum (FBS) (Seradigm cat #1400-500)
Sodium Azide (Sigma cat # S8032)
Brefeldin A (Sigma cat # B7651) in stock solution 10 mg/ml in DMSO stored at −80° C. in aliquots
EDTA (Sigma cat # E7889)
DMSO (Sigma cat # D2650)
Staining buffer (SB) (PBS+10% FBS+0.1% (w/v) Sodium Azide)
RPMI+10% FBS (RPMI/10)
Caltag Fix/Perm Medium A (Invitrogen cat # GAS001S100)
Caltag Fix/Perm Medium B (Invitrogen cat # GAS002S100)
EDTA solution (PBS+0.02% (w/v) EDTA)
Stimulation Reagents:
CMV pp65 peptide pool (JPT cat # PM-PP65-2) (25 pg/peptide, re-suspended in 40 μl DMSO+210 μl PBS, and aliquoted in 10 μl aliquots and stored at −80° C.). JPT product data sheet, incorporated herein by reference, explains that this peptide mix has 138 peptides from human CMV, strain AD169, pp65 antigen (Swiss Prot ID No. P06725), supplied as trifluoroacetate salts with instructions to dissolve in pure DMSO and dilute with PBS buffer.
CMV IE1 peptide pool (JPT cat # PM-IE1) (25 μg/peptide, re-suspended and aliquoted as described for pp65 peptide). JPT product data sheet, incorporated here by reference, explains that this peptide mix has 120 peptides from human CMV, strain AD169, IE1 antigen (Swiss Prot ID No. P13202), supplied as trifluoroacetate salts with instructions to dissolve in pure DMSO and dilute with PBS buffer.
SEB (Toxin Tech cat # BT202) (re-suspended at 100 μg/ml in distilled H2O and aliquoted at −80° C.).

Co-Stimulation Reagents:
Anti-CD28 antibody pure (Becton Dickinson (BD) cat #348040) 0.5 mg/mL
Anti CD49d antibody pure (BD cat #340976) 1.0 mg/ml
Staining Reagents (monoclonal antibodies and live/dead discrimination):

| | |
|---|---|
| Live/Dead Aqua | Life Technologies cat # L34957 |
| CD3 AF700 | BD cat # 557943 |
| CD4 BV786 | Biolegend cat # 317442 |
| CD8 BV711 | Biolegend cat # 301044 |
| CD14 PE-CY5 | eBioscience cat # 15-0149-42 |
| CD16 PE-CY5 | BD cat # 555408 |
| CD19 PE-CY5 | BD cat # 555414 |
| CD56 PE-CY5 | BD cat # 555517 |
| IFNγ BV650 | BD cat # 563416 |
| IL-2 APC | BD cat # 341116 |
| MIP1β APC-Cy7 | BD cat # 561280 |
| TNFα PE-Cy7 | BD cat # 557647 |

Protocol
1. Determine a minimum number of wells needed, based on the number of samples and controls to be analyzed. (Use at least 1 Million (106) cells per well).
SAMPLE WELLS
  a) Unstimulated
  b) SEB-stimulated
  c) CMV pp65 peptide-stimulated
SINGLE STAINED CONTROL WELLS (ADD THESE CELLS AT STEP 29)
*Reserve PBMCs for unstained and surface markers (or use healthy donor)
Blood Sample Preparation:
2. Obtain a blood sample from subjects to be tested. Isolate PBMC via Ficoll gradient centrifugation.
3. Wash PBMC with 10 ml PBS in a 15 mL conical tube.
4. Centrifuge for 5 minutes at 1400 rpm (~450×g) at room temp and decant.
5. Re-suspend cell pellet in 10 ml PBS and count cells.
6. Centrifuge for 5 minutes at 1400 rpm (~450×g) at room temp and decant.
7. Re-suspend cells in needed amount of RPMI/10 media at concentration of 1×10$^6$PBMCs/200 μl RPMI media per well in a 96 well v-bottom plate.
8. Recover the cells in 37° C. 5% $CO_2$ incubator for a minimum of 12-18 hours (e.g., overnight).
9. Centrifuge for 5 minutes at 1600 rpm (~600×g) at room temperature and decant.
Blood Sample Stimulation
10. Re-suspend cells in 190 μl (per well) RPMI media containing 2 μl anti-CD28 antibody (0.5 ug/ml) and 0.5 μl anti-CD49d antibody (1.0 ug/ml) (per well)
11. Add one stimulation per well selected from (a)-(d). (For the viral antigen stimulation, co-stimulation with pp65 and 1E1 antigens also is possible):
  (a) Unstimulated well (gets no stimulants)
  (b) staphylococcal enterotoxin B (SEB)=10 μl of 100 μg/ml (SEB bacterial superantigen serves as positive control)
  (c) CMV pp65 peptide pool JPT=2 μl in sample (reconstituted at 100 ng/ul)
  (d) CMV IE1 peptide pool JPT=2 μl in sample (reconstituted at 100 ng/ul)
12. Incubate at 37 degrees in 5% $CO_2$ incubator for 30 minutes.

13. Add 5 ul of diluted Brefeldin A to each well (dilute stock with RPMI/10 at 1:25=10 μl Bref A+ 240 μl RPMI/10).

14. Incubate for 6 hours at 37° C. in 5% $CO_2$ incubator.

Post-Stimulation Preparation and Antigen Staining

15. Centrifuge cells for 5 min at 1600 rpm (~600×g) room temperature and decant.

16. Re-suspend/Wash with 200 ul PBS.

17. Centrifuge for 5 min at 1600 rpm (~600×g) room temp) and decant.

18. Re-suspend cells in 180 μl of 0.02% EDTA in PBS (from 4 degree, keep on ice until just before use) and incubate in 37° C. for 10 min.

19. Re-suspend in 50 μl Staining Buffer (SB), then add the following reagents to each well:
   CD4: 2 μl
   CD8: 3 μl
   CD14: 0.5 μl
   CD16: 1 μl
   CD19: 2 μl
   CD56: 4 μl
   LIVE/Aqua: 0.2 μl Mix and incubate for 30 minutes in dark at 4° C.

These markers are useful as follows: CD3– to identify T cells; CD4– to identify CD4+ T cell subset of CD3+ T cells; CD8– to identify CD8+ T cell subset of CD3+ T cells; CD14– to exclude monoctyes from analysis; CD16– to exclude natural killer cells from analysis; CD19– to exclude B cells from analysis; CD56– to exclude natural killer cells from analysis.

20. Add 150 μl SB, spin (5 min, 1600 rpm (~600×g), room temp) and decant.

21. Re-suspend in 200 μl SB, spin (5 min, 1600 rpm (~600×g), room temp) and decant.

22. Re-suspend in 100 μl of Caltag Fix/Perm Medium A in ALL wells for 20 minutes in dark at room temperature.

23. Spin down (5 min, 2000 rpm (~930×g), room temp) and decant.

24. Wash with 200 μl SB, spin down (5 min, 2000 rpm (~930×g), room temp) and decant.

25. Re-suspend with 100 μl Caltag Fix/Perm Medium B in ALL wells.

26. Add each of the following antibodies to each test sample well for 20 min in dark at room temp:
   IL-2: 3 μl
   IFNγ: 3 μl
   TNFα: 3 μl
   MIP1β: 3 μl
   CD3: 2 μl 27. Spin down (5 min, 2000 rpm (~930×g), room temp) and decant.

28. Wash with 200 μl SB.

29. Add single-stained control wells to the plate, using healthy donor cells or cells reserved from the day before, or compensation beads for individual cytokines (1 drop each of compensation antibody capture beads BD #552843)—stain in 50 μl SB.

30. Add 150 μl SB spin down (5 min, 2000 rpm (~930×g), room temp) and decant.

31. Wash samples with 200 μl SB.

32. Re-suspend ALL WELLS in 200 μl of PBS for flow cytometer analysis.

Flow Cytometry

Flow cytometry was performed with cell selection and gating substantially as described above.

EXAMPLE 2

Overview/Synopsis

The inventors have applied higher-order functional cytokine flow cytometry (CFC) to the assessment of clinical risk in immune-compromised (hematopoietic cell transplant, HCT) patients using a protocol essentially as outlined above in Example 1.

Peripheral blood mononuclear cells (PBMC) were isolated from blood samples drawn from thirty HCT recipients at day +30 after HCT. Based on monitoring for CMV reaction for period of thirty months, the HCT recipients were divided into three groups: Group 1: "Elite Controllers"—subjects with no observed CMV reactivation for 30 months following HCT; Group 2 "Spontaneous Controllers"—subject who experienced low level CMV reactivation, but the reactivation resolved without anti-viral therapy; and Group 3: "Non-controllers"—subjects who experienced higher level, uncontrolled CMV reactivation viremia requiring anti-viral therapy. The CMV serostatus of the hematopoietic cells did not appear to strongly correlate with CMV viremia in the subject sample studied.

Cryopreserved PBMC from the +30 day sample were thawed, stimulated with peptide pools spanning CMV tegument protein pp65, and then analyzed for lineage, cell surface phenotype, and the production of four cytokines/chemokines: TNFα, IFNγ, IL-2 and MIP-1β.

Interferon gamma has been investigated as a predictive marker for CMV viremia, but IFNγ measurements gave poor discrimination in the subjects studied.

Cytokine signatures of the pp65-stimulated CD8+ T cells drawn at day +30 were examined. Two cytokine/chemokine signatures were identified that positively or negatively correlated with failure to control CMV after HCT. The signature of polyfunctional cells (e.g., CD8+ T cells producing all four effector proteins: TNFα+/IFNγ+/IL-2+/MIP-1β+) was associated with CMV control (the "protective signature" or PS or PHENOTYPE P). Conversely, TNFα-negative/IFNγ+/IL-2-negative/MIP-1β+ cells were positively correlated with risk of viremia ("nonprotective signature" or NPS or PHENOTYPE N). Each of these phenotypes alone was useful to discriminate subjects more or less likely to experience CMV reactivation in the first 100 days post-transplant. "High" versus "Low" cutoff used was 10% of responsive T cells, as described above. "High" versus "Low" cutoff used with 2% of responsive T cells, as described above.

By combining these two positive and negative signatures, into one predictive algorithm, they accurately predicted risk of CMV. (See FIGS. 18A-18D.) In the test group of 30 HCT subjects, the combination of low PS (<2%) and high NPS numbers (>10%) correlated with high risk of reactivation, with 8/10 (80%) of patients this signature reactivating CMV. In contrast, we observed a far lower incidence of reactivation, with just 2/20 (10%) patients who lacked this immune phenotype reactivating CMV within 100 days after HCT (p=0.0002).

EXAMPLE 3—CMV RISK STRATIFICATION

Example 3 extends the initial results from Example 2 by incorporation of a larger sample of patients.

Overview/Synopsis

The inventors have applied higher-order functional cytokine flow cytometry (CFC) to the assessment of clinical risk in immune-compromised (hematopoietic cell transplant, HCT) patients using a protocol essentially as outlined above in Example 1.

Figure 7:
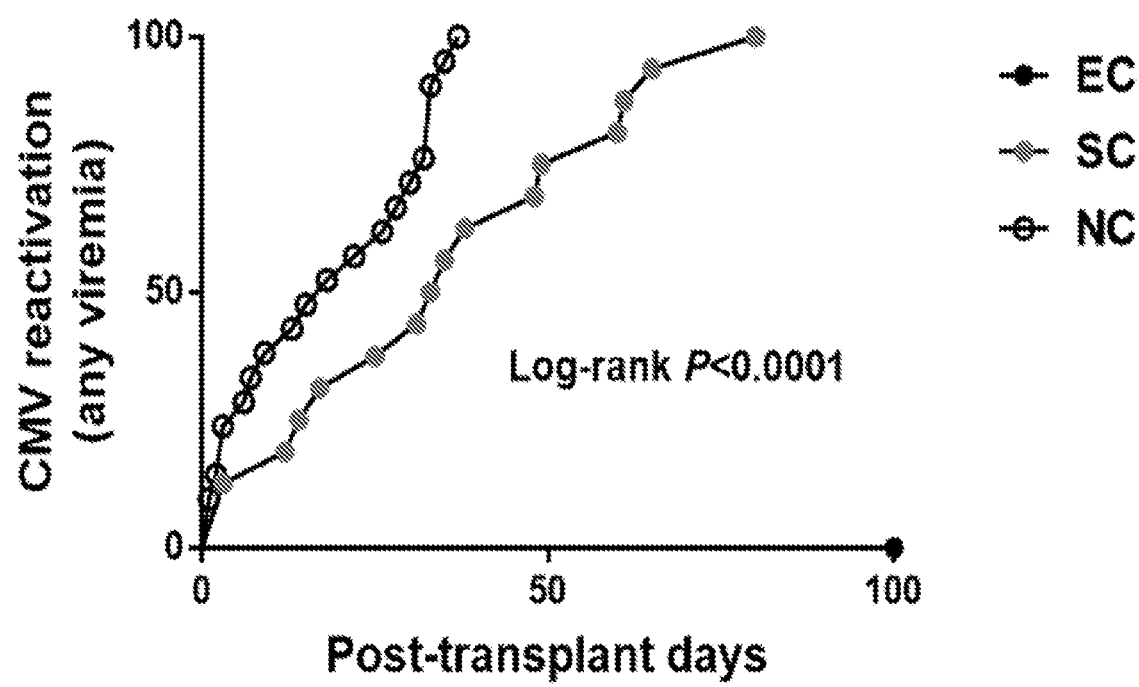
FIG. 7 depicts a graph of cumulative incidence of CMV reactivation by CMV group. EC, elite controllers (n=19); SC, spontaneous controllers (n=16); NC, non-controllers (n=21).
Figure 8:
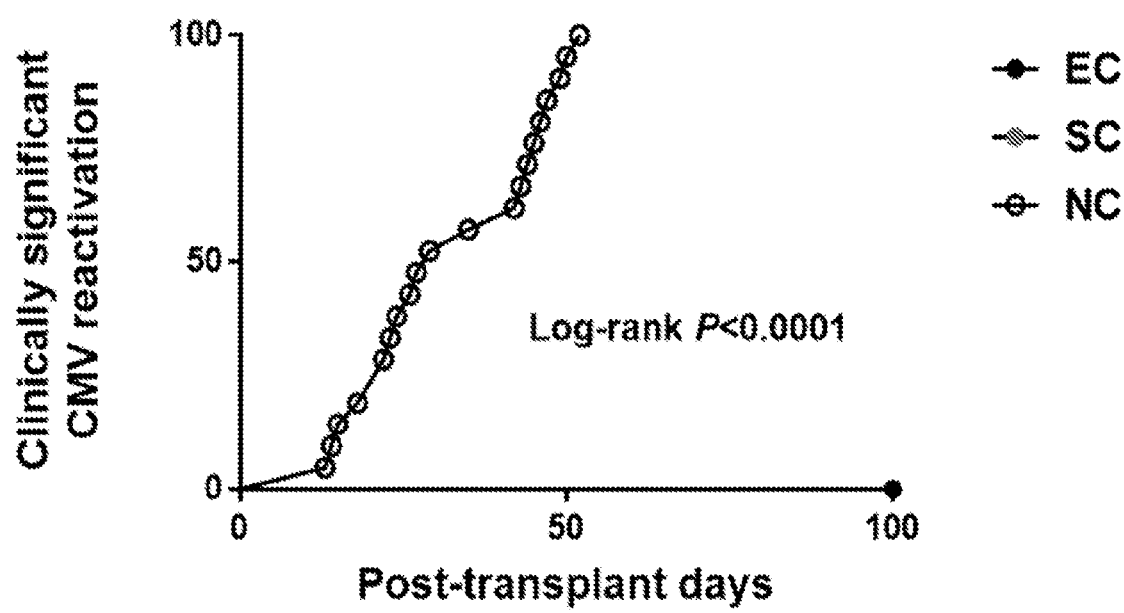
FIG. 8 depicts a graph of cumulative incidence of CMV reactivation requiring treatment. EC, elite controllers (n=19); SC, spontaneous controllers (n=16); NC, non-controllers (n=21).
Figure 9:
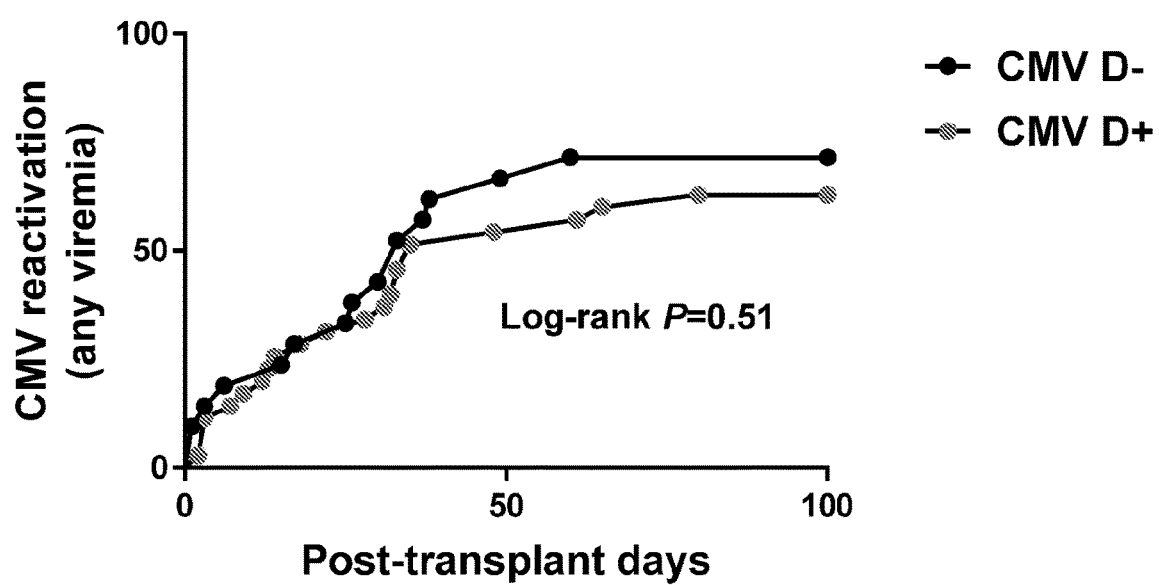
FIG. 9 depicts a graph of cumulative incidence of CMV reactivation by CMV donor serostatus. Cohort was stratified based on whether the subject received transplant from CMV seropositive (D+; n=21) or CMV seronegative (D−; n=35) donor.
Figure 10:
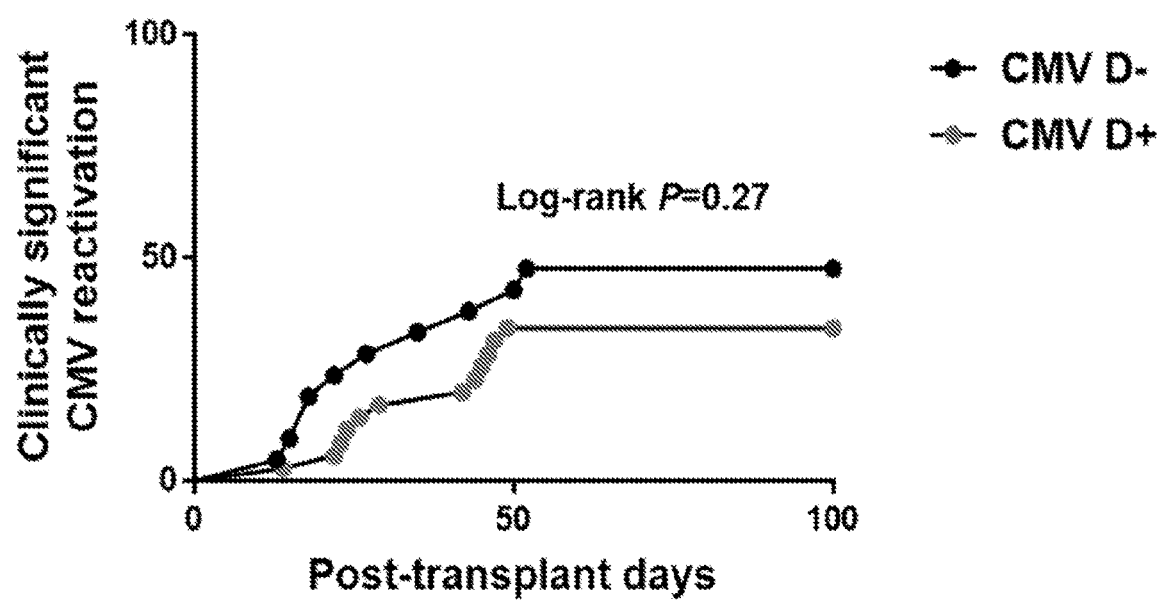
FIG. 10 depicts a graph cumulative incidence of CMV reactivation requiring treatment by CMV donor serostatus. Cohort was stratified based on whether the subject received transplant from CMV seropositive (D+; n=21) or CMV seronegative (D−; n=35) donor.

Peripheral blood mononuclear cells (PBMC) were isolated from blood samples drawn from fifty-six HCT recipients at day +30 after HCT. Based on monitoring for CMV reaction for period of thirty months, the HCT recipients were divided into three groups: Group 1: "Elite Controllers"— subjects with no observed CMV reactivation for 30 months following HCT; Group 2 "Spontaneous Controllers"—subject who experienced low level CMV reactivation, but the reactivation resolved without anti-viral therapy; and Group 3: "Non-controllers"—subjects who experienced higher level, uncontrolled CMV reactivation viremia requiring anti-viral therapy. (See FIGS. 7 and 8.) The CMV serostatus of the donor did not appear to strongly correlate with CMV viremia in the subject sample studied. (See FIGS. 9 and 10.)

Cryopreserved PBMC from the +30 day sample were thawed, stimulated with peptide pools spanning CMV tegument protein pp65, and then analyzed for lineage, cell surface phenotype, and the production of four cytokines/chemokines: TNFα, IFNγ, IL-2 and MIP-1β.

Figure 2:
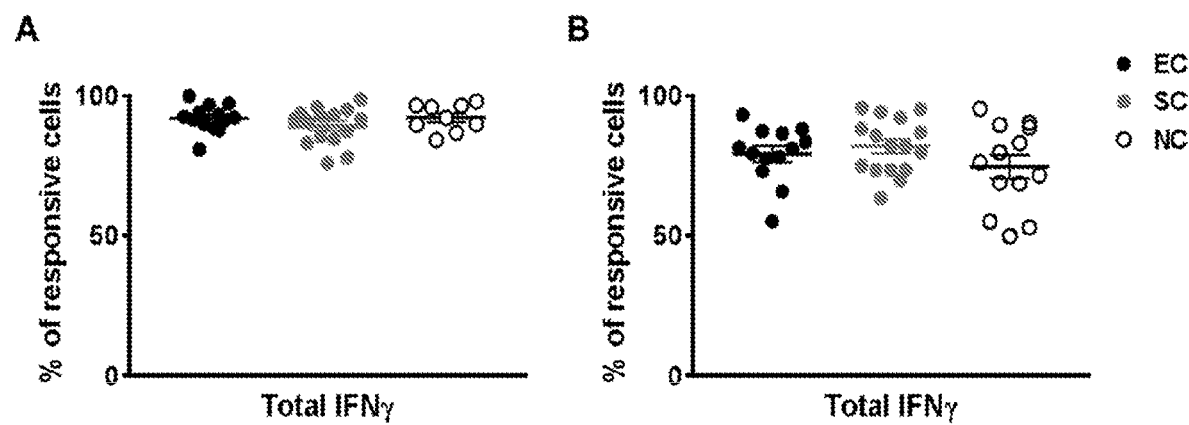
FIG. 2 is a scatter plot of Interferon gamma (IFNγ) production across patient groups.
Figure 11:
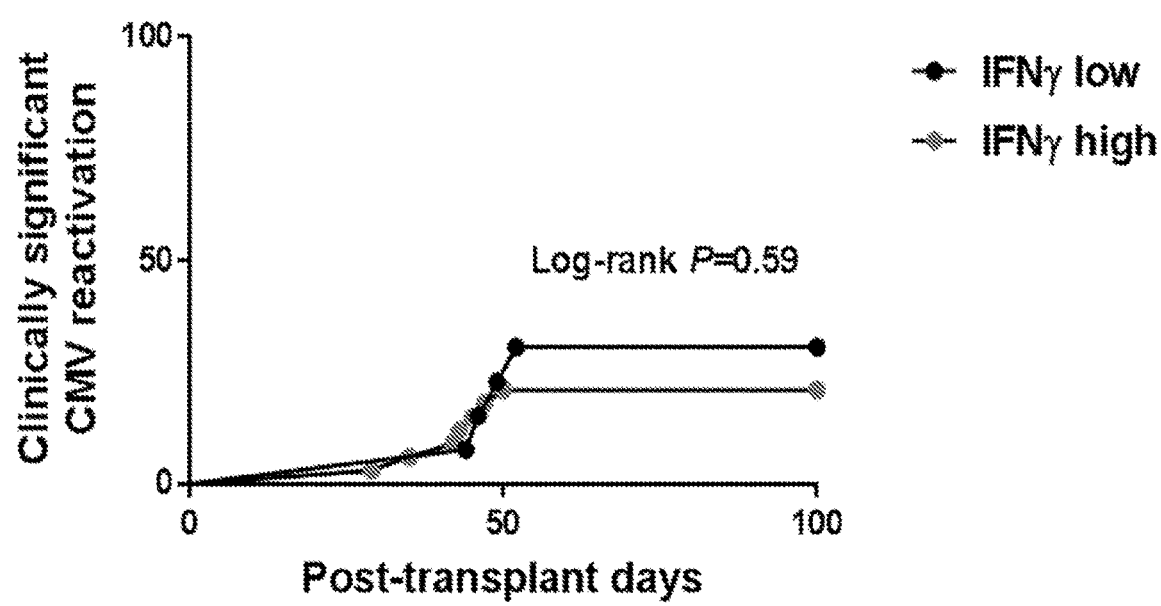
FIG. 11 depicts a graph of cumulative incidence of clinically significant CMV reactivation (CMV disease or CMV viremia requiring therapy) by levels of IFNγ

Interferon gamma has been investigated as a predictive marker for CMV viremia, but IFNγ measurements gave poor discrimination in the subjects studied. (See FIGS. 2 and 11.)

Figure 12:
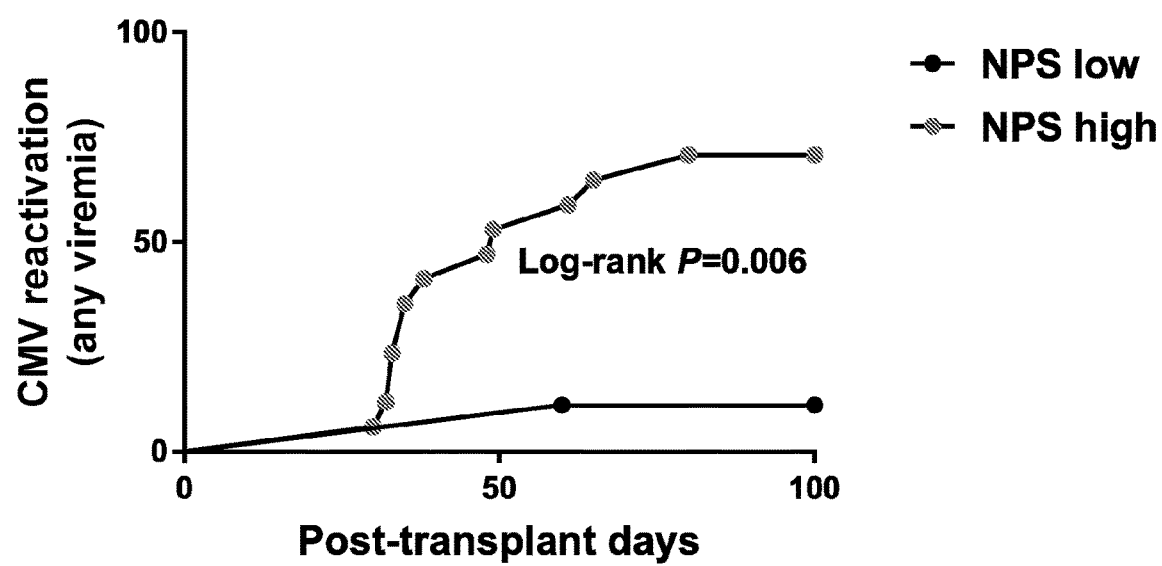
FIG. 12 depicts the cumulative incidence of CMV reactivation (any viremia) by levels of the non-protective signature. Cohort was stratified based on whether the subject blood sample exhibited high vs. low levels of the NPS signature (IL2−IFNγ+TNFα−MIP1β+ cells within the CMV (pp65)-specific CD8+ T cell compartment).
Figure 13:
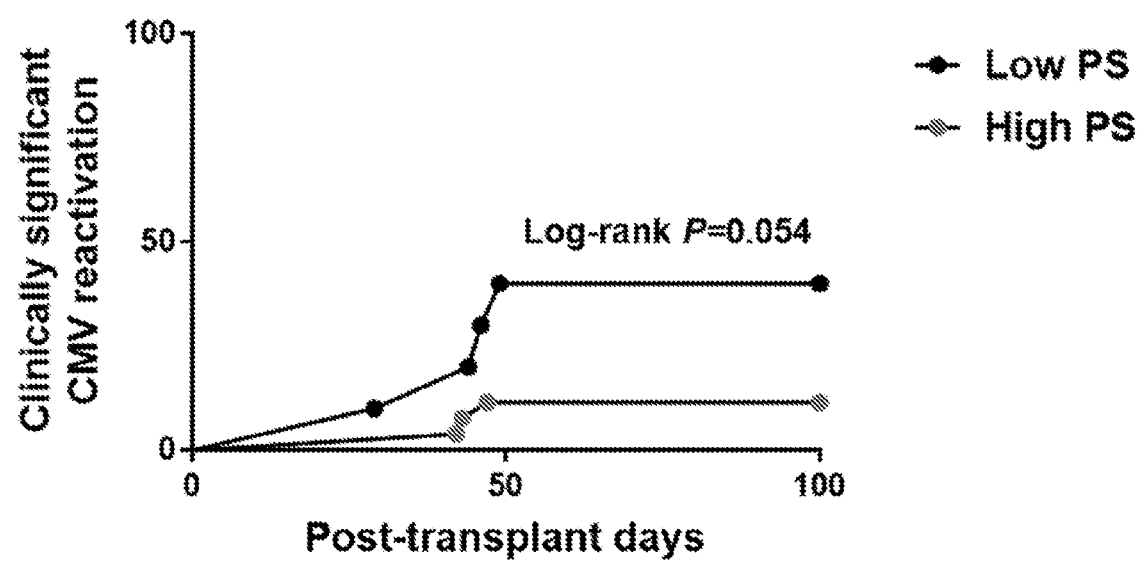
FIG. 13 depicts the cumulative incidence of clinically significant CMV reactivation (CMV disease or CMV viremia requiring therapy) by levels of protective signature. Cohort was stratified based on whether the subject blood sample exhibited high vs. low levels of the PS signature (IL2+IFNγ+TNFα+MIP1β+ cells within the CMV(pp65)-specific CD8+ T cell compartment).
Figure 14:
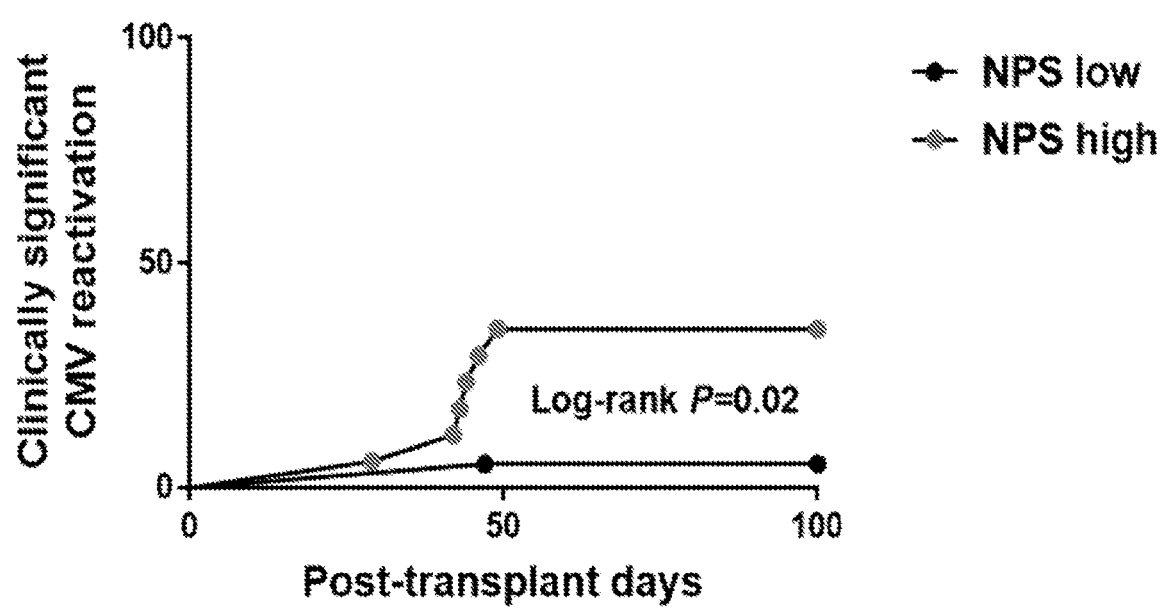
FIG. 14 depicts the cumulative incidence of clinically significant CMV reactivation (CMV disease or CMV viremia requiring therapy) by levels of non-protective signature. Cohort was stratified based on whether the subject blood sample exhibited high vs. low levels of the NPS signature (IL2−IFNγ+TNFα−MIP1β+ cells within the CMV (pp65)-specific CD8+ T cell compartment).
Figure 15:
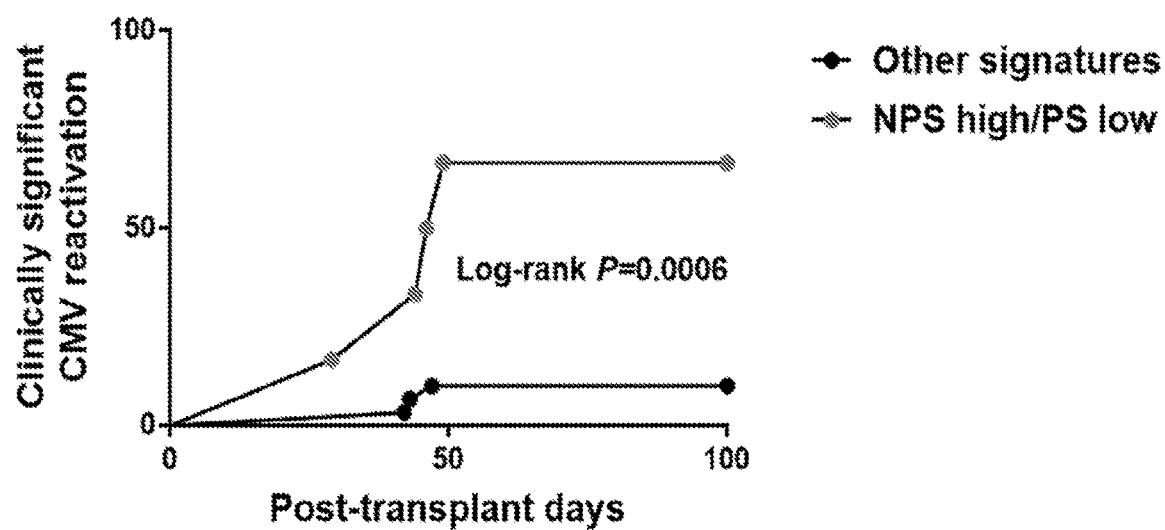
FIG. 15 depicts the cumulative incidence of CMV reactivation requiring therapy grouped by a composite biomarker combining high levels of the non-protective signature and low levels of the protective signature as compared to all other signatures. Cohort stratified based on whether the subject blood sample exhibited a composite bio-marker consisting of high levels of the NPS (IL2−IFNγ+TNFα−MIP1β+ cells within the CMV(pp65)-specific CD8+ T cell compartment) and low levels of the PS (IL2+IFNγ+TNFα−MIP1β+ cells within the CMV(pp65)-specific CD8+ T cell compartment) vs. all other signatures.

Cytokine signatures of the pp65-stimulated CD8+ T cells drawn at day +30 were examined. Two cytokine/chemokine signatures were identified that positively or negatively correlated with failure to control CMV after HCT. The signature of polyfunctional cells (e.g., CD8+ T cells producing all four effector proteins: TNFα+/IFNγ+/IL-2+/MIP-1β) was associated with CMV control (the "protective signature" or PS or PHENOTYPE P). Conversely, TNFα-negative/IFNγ+/IL-2-negative/MIP-1β+ cells were positively correlated with risk of viremia ("nonprotective signature" or NPS or PHENOTYPE N). Each of these phenotypes alone was useful to discriminate subjects more or less likely to experience CMV reactivation in the first 100 days post-transplant. Data analysis for the NPS T cell phenotype is set forth in FIG. 12. "High" versus "Low" cutoffs were identified using the most significant p value approach for each biomarker and outcome. Protective signature 'PS' T cell phenotype in FIG. 13 associated with CMV activation requiring therapy.

What is claimed is:

1. A method comprising:
   (a) identifying or quantifying a risk for reactivation of a latent *herpesviridae* virus in an immune-compromised mammalian subject from measurement of a T cell subset from a blood sample isolated from the subject, wherein the measurement of the T cell subset is obtained by
      (i) exposing the T cells to one or more antigens from the latent *herpesviridae* virus, under conditions to stimulate a T cell immune response;
      (ii) evaluating individual T cells to detect or measure expression of cytokines IL-2, IFNγ, TNFα, and MIP-1β in the individual T cells;
      (iii) evaluating the individual T cells to detect or measure CD8 expression; and
   quantifying T cells having a CD8-positive (CD8+), IL-2-positive (IL-2+), IFNγ-positive (IFNγ+), TNFα-positive (TNFα+), MIP-1β-positive (MIP-1β+) phenotype ("PHENOTYPE-P") from the blood sample; and/or quantifying T cells having a CD8-positive (CD8+), IL-2-negative (IL-2−), IFNγ-positive (IFNγ+), TNFα-negative (TNFα−), MIP-1β-positive (MIP-1β+) phenotype ("PHENOTYPE-N") from the blood sample, wherein the quantifying comprises:
      quantifying the T cells with the phenotype relative to total T cells analyzed, to generate a relative measure of the quantity of the T cells with the phenotype; and/or
      calculating a relative percentage or ratio of PHENOTYPE-P T cells to PHENOTYPE-N T cells;
   (b) identifying an elevated or high risk for reactivation of the virus in the subject from the measurement; and
   (c) administering, to the subject identified as having the elevated or high risk of viral reactivation, a prophylaxis that comprises an antiviral chemotherapeutic agent, wherein said agent comprises Ganciclovir, Valganciclovir, Foscarnet, Cidofovir, Maribavir, Brincidofovir, or Letermovir.

2. The method according to claim 1, wherein the mammalian subject is human.

3. The method according to claim 1, wherein the subject is a transplant recipient, and wherein the identifying or quantifying risk is performed on a blood sample comprising the T cells obtained from the subject 14 or more days after the transplant.

4. The method according to claim 3, wherein the transplant recipient is an allogeneic organ transplant recipient, an allogeneic tissue transplant recipient, or an allogeneic cell transplant recipient.

5. The method according to claim 4, wherein the subject is a hematopoietic cell transplant recipient.

6. The method according to claim 1, wherein the subject is immune-compromised from cancer chemotherapy or immunosuppressant therapy.

7. The method according to claim 1, wherein the blood sample is a never-frozen blood sample comprising T cells.

8. The method according to claim 1 wherein the method comprises said measuring of the expression of the cytokines.

9. The method according to claim 8, wherein the one or more antigens comprises a latent *herpesviridae* virus viral envelope protein antigen, or comprises one or more antigenic fragments thereof.

10. The method according to claim 8, wherein the latent virus is CMV, and the one or more antigens comprises CMV tegument phosphoprotein 65 (pp65), or CMV immediate early 1 (IE1) protein, or comprises one or more antigenic fragments thereof, or comprises mixtures of said proteins or antigenic fragments.

11. The method according to claim 8, wherein the exposing step further comprises exposing the T cells to anti-CD49d and/or anti-CD28 antibodies.

12. The method according to claim 8 that comprises identifying an elevated or high risk of viral inactivation from one or more of the following:

increased percentages of Phenotype-N T cells in the blood sample;

decreased percentages of Phenotype-P T cells in the blood sample; and a combination of a high percentage of Phenotype-N T cells and a low percentage of Phenotype-P T cells in the blood sample.

* * * * *

UNITED STATES PATENT AND TRADEMARK OFFICE
CERTIFICATE OF CORRECTION

PATENT NO. : 11,913,962 B2
APPLICATION NO. : 16/613411
DATED : February 27, 2024
INVENTOR(S) : Krishna Komanduri et al.

It is certified that error appears in the above-identified patent and that said Letters Patent is hereby corrected as shown below:

In the Claims

At Column 29, Line 49, "quantifying" should be -- (iv) quantifying --.

At Column 30, Line 65, "(lE1)" should be -- (IE1) --.

Signed and Sealed this
Tenth Day of September, 2024

Katherine Kelly Vidal
*Director of the United States Patent and Trademark Office*